(12) United States Patent
Greener

(10) Patent No.: US 8,506,945 B2
(45) Date of Patent: *Aug. 13, 2013

(54) POLYMERS WITH STRUCTURE-DEFINED FUNCTIONS

(75) Inventor: Bryan Greener, York (GB)

(73) Assignee: Smith & Nephew, PLC., London (GB)

( * ) Notice: Subject to any disclaimer, the term of this patent is extended or adjusted under 35 U.S.C. 154(b) by 66 days.

This patent is subject to a terminal disclaimer.

(21) Appl. No.: 13/104,360

(22) Filed: May 10, 2011

(65) Prior Publication Data

US 2011/0300096 A1  Dec. 8, 2011

Related U.S. Application Data

(62) Division of application No. 10/490,649, filed as application No. PCT/GB02/04344 on Sep. 25, 2002, now Pat. No. 7,955,594.

(30) Foreign Application Priority Data

Sep. 26, 2001 (GB) .................................. 0123232.1

(51) Int. Cl.
*A61K 31/74* (2006.01)

(52) U.S. Cl.
USPC ...................................................... 424/78.17

(58) Field of Classification Search
None
See application file for complete search history.

(56) References Cited

U.S. PATENT DOCUMENTS

| | | | |
|---|---|---|---|
| 3,576,592 A | 4/1971 | Zviak et al. | |
| 3,649,457 A | 3/1972 | Westman | |
| 4,182,752 A | 1/1980 | Maeda et al. | |
| 5,079,140 A | 1/1992 | Albarella et al. | |
| 5,081,111 A | 1/1992 | Akimoto et al. | |
| 5,378,456 A * | 1/1995 | Tsou | 424/78.3 |
| 5,453,461 A | 9/1995 | Heiliger et al. | |
| 5,489,653 A | 2/1996 | Charles et al. | |
| 5,753,771 A | 5/1998 | Xie | |
| 2002/0055185 A1 | 5/2002 | Minard et al. | |
| 2003/0063998 A1 | 4/2003 | Ghosh et al. | |

FOREIGN PATENT DOCUMENTS

| | | |
|---|---|---|
| GB | A-1 178 364 | 1/1970 |
| GB | A-1 488 486 | 10/1977 |
| JP | 2002-257014 | 9/2002 |

OTHER PUBLICATIONS

Examiner's first report issued Dec. 20, 2006 for Australian Application No. 2002329421, Australian Government, IP Australia, Woden, Australia.

(Continued)

*Primary Examiner* — Paul Dickinson
(74) *Attorney, Agent, or Firm* — Stephen J. Weyer, Esq.; Stites & Harbison PLLC

(57) ABSTRACT

An alternating copolymer comprising a backbone of residues of a maleic anhydride derivative and those of a compound containing vinylic unsaturation, which also comprises residues of an active compound containing a nucleophilic group, bound to the backbone by a residue of the nucleophilic group, including such a copolymer comprising residues of an active compound containing an alcohol, thiol or amine group. The chemical and biological properties of actives, such as protease inhibitors, neurotransmitter drugs, and other small molecule active drugs, are enhanced, and new applications enabled. Also, artefacts, including a solid medical implant device, dressing or scaffold or a fluid adhesive or medicinal composition comprising such a polymer, and a method of use of such a polymer, including a method for the treatment or prophylaxis of wounds.

25 Claims, 14 Drawing Sheets

Inhibition of: trypsin (top) by EXAMPLE 14 (top left) and AEBSF (top right); elastase (middle) by EXAMPLE 14 (middle left) and AEBSF (middle right); thrombin (bottom) by EXAMPLE 14 (bottom left) and AEBSF (bottom right).

(56) References Cited

OTHER PUBLICATIONS

Examiner's report No. 2 issued Aug. 12, 2008 for Australian Application No. 2002329421, Australian Government, IP Australia, Woden, Australia.
Office Action issued Apr. 21, 2009 for Canadian Application No. 2,461,504, Canadian Intellectual Property Office, Ottawa, Ontario, Canada.
Office Action issued Mar. 18, 2010 for Canadian Application No. 2,461,504, Canadian Intellectual Property Office, Ottawa, Ontario, Canada.
Office Action issued Dec. 6, 2010 for Canadian Application No. 2,461,504, Canadian Intellectual Property Office, Ottawa, Ontario, Canada.
Office Action issued Mar. 10, 2008 for European Application No. 02 765 048.0-2109, European Patent Office, Munich, Germany.
Office Action issued Jan. 16, 2009 for European Application No. 02 765 048.0-2109, European Patent Office, Munich, Germany.
Office Action issued Oct. 16, 2009 for European Application No. 02 765 048.0-2109, European Patent Office, Munich, Germany.
Office Action issued Jan. 27, 2011 for European Application No. 02 765 048.0-2109, European Patent Office, Munich, Germany.
English translation of Office Action issued Jun. 10, 2008 for Japanese Application No. 2003-530739, Nogawa Patent Office, Osaka, Japan.
English translation of Office Action issued May 7, 2009 for Japanese Application No. 2003-530739, Shiga International Patent Office, Tokyo, Japan.

* cited by examiner

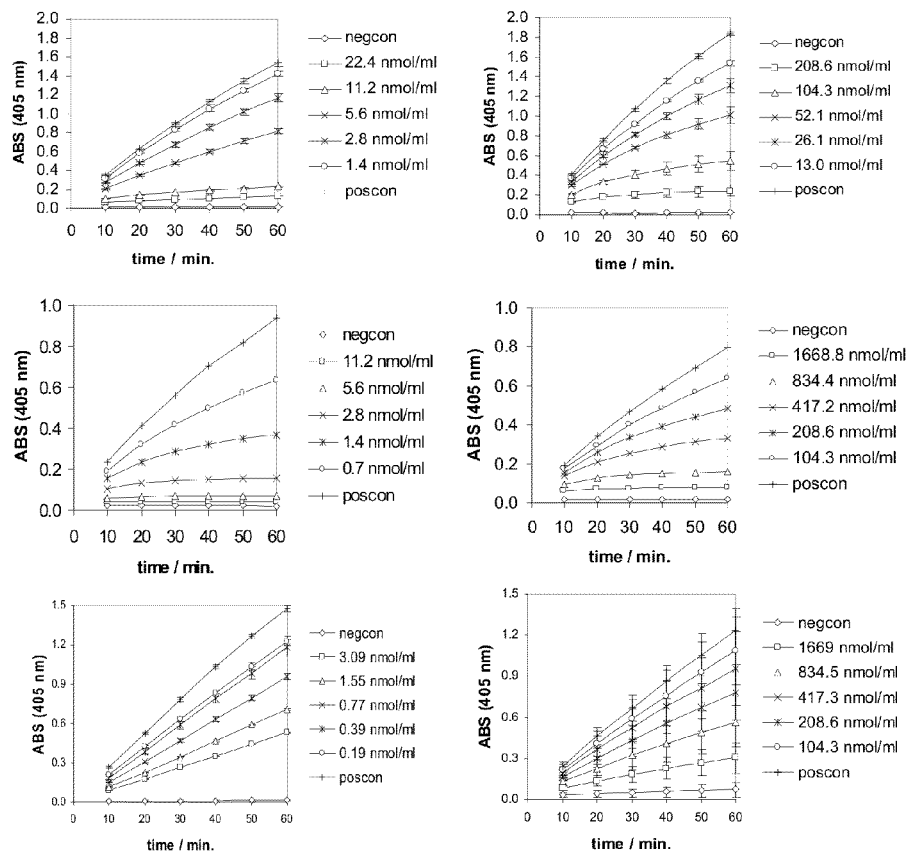
Figure 1   Inhibition of: trypsin (top) by EXAMPLE 14 (top left) and AEBSF (top right); elastase (middle) by EXAMPLE 14 (middle left) and AEBSF (middle right); thrombin (bottom) by EXAMPLE 14 (bottom left) and AEBSF (bottom right).

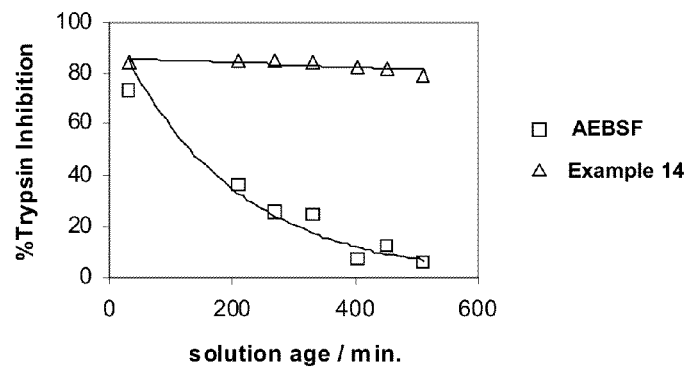
Figure 2    Inhibition of trypsin by aged inhibitor solutions (0.2M TRIS pH 8, 20 $^0C$).
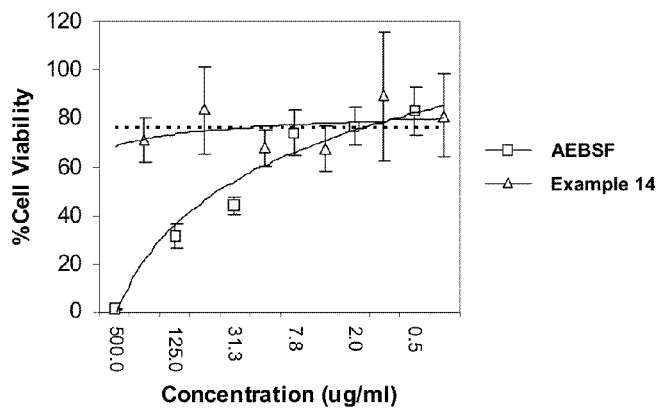
Figure 3    Cytotoxicity profiles of AEBSF and Example 14 on a culture of Ovine Meniscal Chondrocytes P3 after 48 h incubation time. Broken line represents averaged vehicle only values.

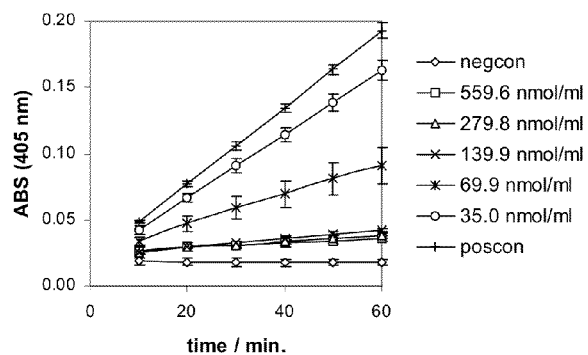
Figure 4     Inhibition of elastase by Example 14 in the presence of excess heat inactivated foetal calf serum.
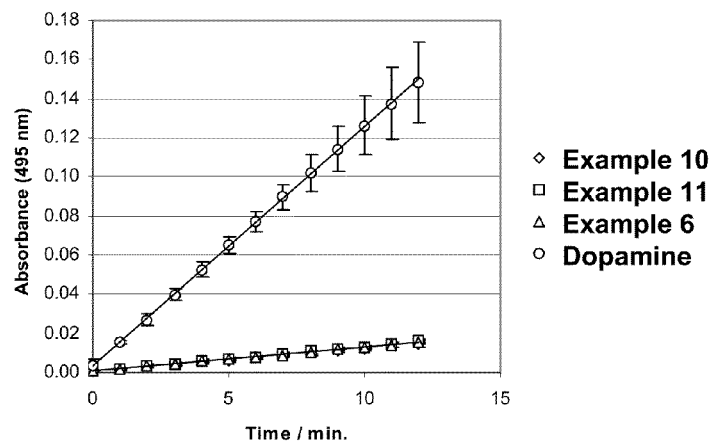
Figure 5     Oxidative degradation of Example 6, Example 10, Example 11 and Dopamine (0.2 M TRIS pH 8, 25 $^0$C).

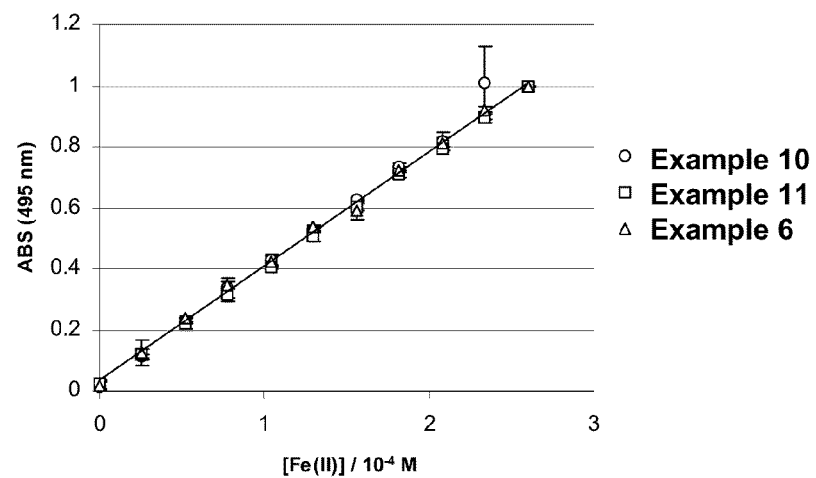
Figure 6      Complexation of iron ions by Example 6, Example 10 and Example 11 (0.2 M TRIS pH 8, 25 °C).
Figure 7      Image of the equimolar complex of Example 22 and heparin.

Figure 8     Image of the equimolar complex of Example 22 and 5-(2-aminoethylamino)-1-naphthalene sulfonic acid, sodium salt derivatised maleic anhydride-alt-iosbutylene copolymer.

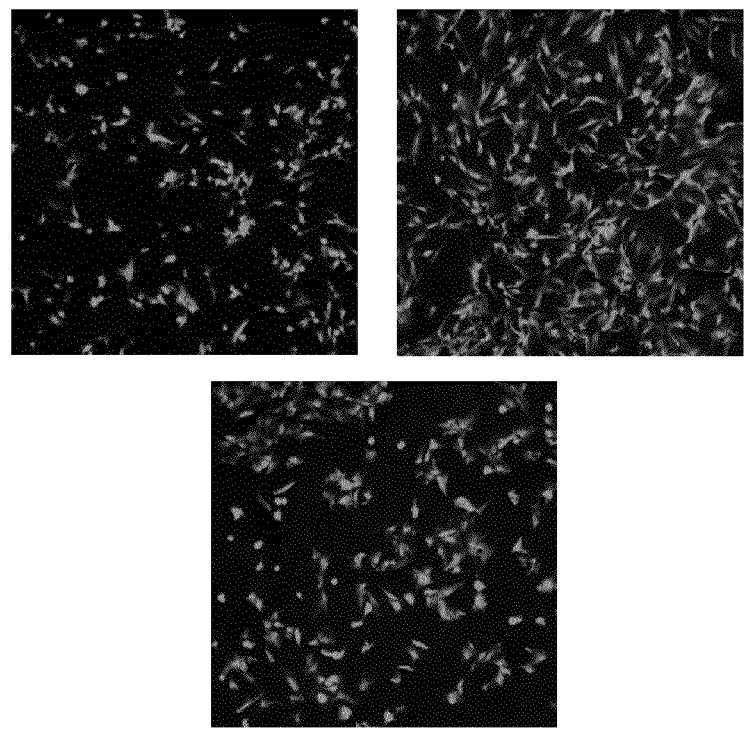
Figure 9 Attachment of human dermal fibroblasts to Example 23 (top left), Example 31 (top right) and Example 30 (bottom) following 2 h incubation.

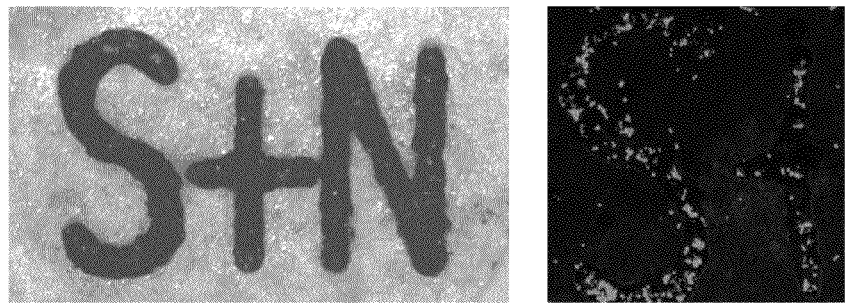
Figure 10  Laser designated patterning of the surface of a disc of Example 23 (left) and subsequent attachment of human dermal fibroblasts to the designated area (right).
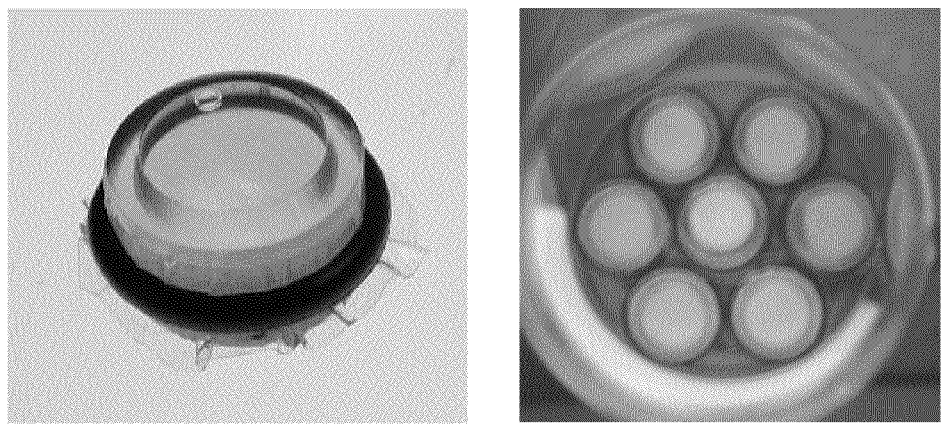
Figure 11  Dialysis button assembly (left) and fluorescent emission (493 nm) from the experimental group of buttons under UV light illumination (365 nm) (right).

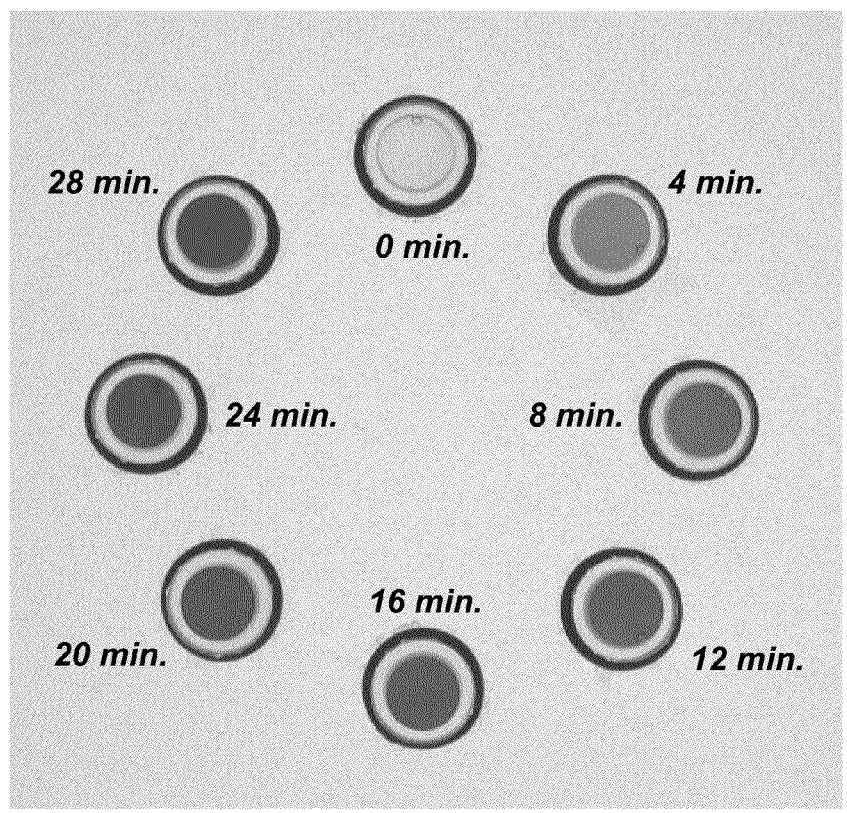
Figure 12  Image of the full dialysis time-course. Each button, containing 100 µl of polymer conjugate (10 mg/ml in 0.2 M TRIS pH8) was immersed in 5 ml sodium periodate solution (5 ml, 94 mM) at 25 °C.

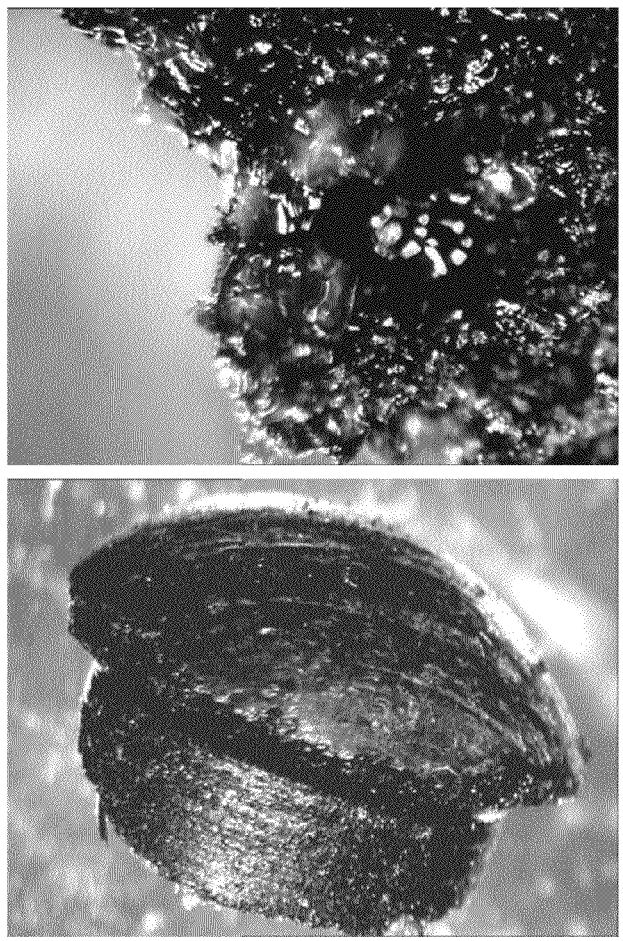
Figure 13   Image of the porosity of Example 30, produced by condensing Example 22 (top) and a screw head produced by moulding Example 30 (bottom).

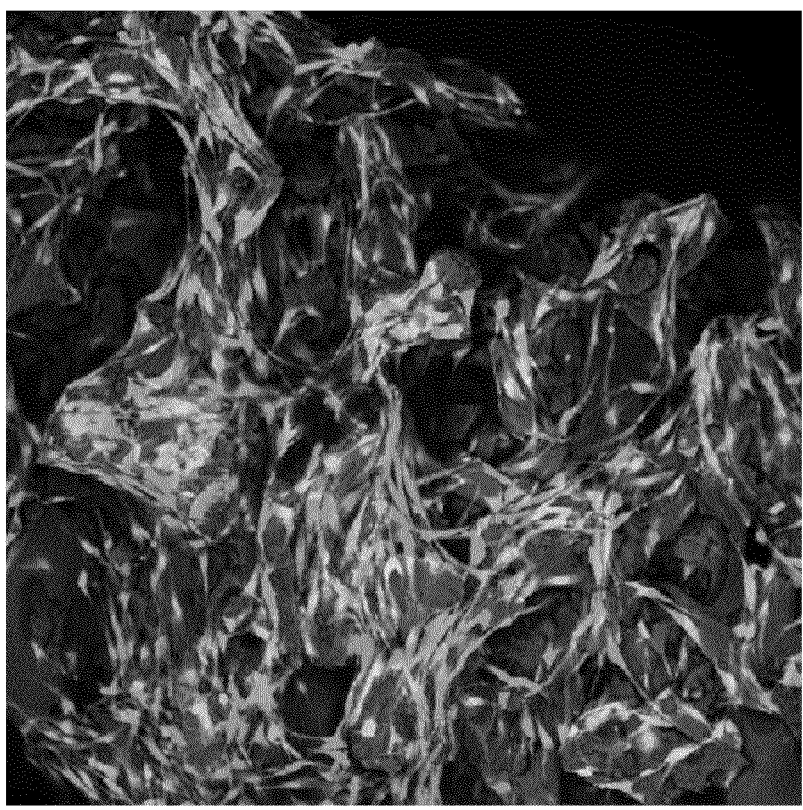
*Figure 14*  *Image of cell-seeded scaffold (human dermal fibroblasts) after 6 days incubation*

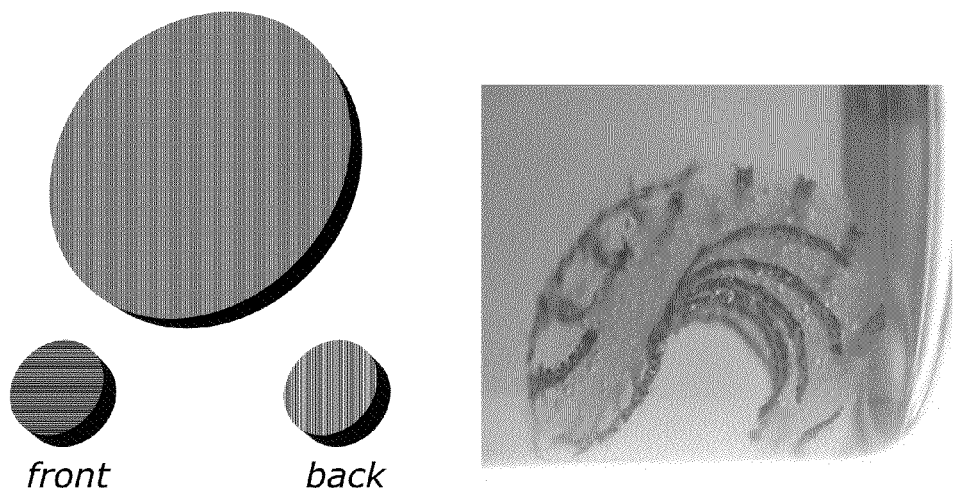
Figure 15      Self-forming device shape created from a 6 mm diameter flat circular disc of Example 22, laser patterned (left) and swollen in Dulbecco's Modified Eagle's Medium (right).

POLYMERS WITH STRUCTURE-DEFINED FUNCTIONS

CROSS REFERENCE TO RELATED APPLICATIONS

This application is a divisional of application Ser. No. 10/490,649 filed Sep. 8, 2004, now U.S. Pat. No. 7,955,594 which is the National Stage of International Application No. PCT/GB2002/004344, filed Sep. 25, 2002 (which is hereby incorporated by reference).

This invention relates to functional polymers of precise molecular architecture. These architectures can by systematically varied to control the local environment around pendant active moieties. These moieties can be capable of sequestering ionic or molecular species from the local environment or interacting with biomolecules.

The invention further relates to precursors therefor and to artefacts made therefrom such as solid devices, e.g. medical implant devices, dressings or scaffolds for the enhancement of repair processes or accelerated healing. Furthermore the devices may be non-degradable or fully degradable or bioresorbable. Such artefacts also include fluid compositions, such as adhesives, and medicinal compositions suitable for management of the wound environment, in situ or ex situ.

More particularly, the invention relates to functional polymeric materials that can be processed into a number of physical forms such as solid forms, e.g. films, fibres and constructs, and fluid compositions, such as medicinal compositions, including those suitable for management of the wound environment, in situ or ex situ.

In one class of traditional polymer-based functional materials, the materials comprise a polymer to which chemically functional appendages have been covalently bonded. In this case, the polymer acts merely as an anchor for the functional group, as shown in FIG. 16.

This approach has been widely applied to immobilise enzymes and small molecule actives (often physiologically active molecules) on a material while still retaining much of their functional activity.

In such functionalised materials, functional activity is entirely dependent upon the type of chemical function attached to the material and the extent of functionalisation. It is also noted that the ultimate function of a material can be altered by first altering the chemical function to be attached.

However, for molecules with complex function, such structural and/or functional alteration is not always possible and frequently results in de-activation or loss of chemical or physiological function. To overcome these limitations and retain control over the rate of function and selectivity of a functional material, it would be desirable to control the function of the material without altering the structure of the chemically active appendage. The present invention provides a solution to this technical problem.

An object of the present invention is the preparation of functional polymers in which the extent and specificity of function of an appended functional species is determined by the immediate surrounding polymer structure, as illustrated schematically in FIG. 17.

To achieve this aim, we have selected a polymer system that allows control of substituent type at four adjacent and regularly repeating sites, as illustrated in FIG. 18.

It is to one or more of these positions that the chemically functional appendage is specifically attached.

In accordance with a first aspect of the present invention there is provided an alternating copolymer comprising a backbone of residues of a maleic anhydride derivative and those of a compound containing vinylic unsaturation, characterised in that it also comprises residues of an active compound containing a nucleophilic group, bound to the backbone by a residue of the nucleophilic group.

In a class of copolymers of the present invention there is provided an alcohol, thiol or amine substituted copolymer comprising residues of a maleic anhydride derivative and those of a compound containing vinylic unsaturation.

That is, such a copolymer comprising residues of a maleic anhydride derivative and those of a compound containing vinylic unsaturation, characterised in that it also comprises residues of an active compound containing an alcohol, thiol or amine group, bound to the backbone by a residue of the nucleophilic group. These may be the product of reaction at the anhydride moiety, with an alcohol-, thiol-, isocyanate- or amine-derivatised chemically functional compound.

The backbone of the polymers of the invention is the result of geometrically specific, alternating radical copolymerisation of maleic anhydride derivatives (A) with vinyl derivatives (B) (see Trivedi, B. C., *Maleic Anhydride*, Plenum Press NY, 1982). For example, the well-known polymerisation of maleic anhydride and ethylene:

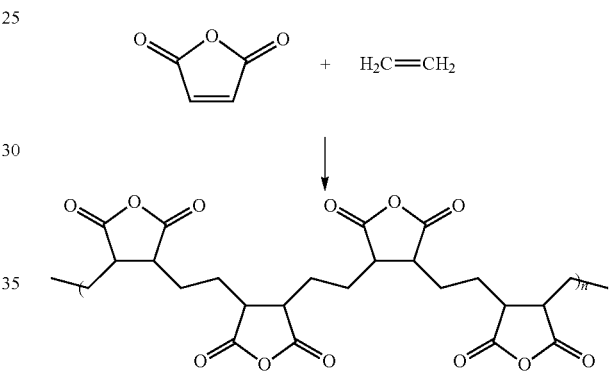

The selection of suitable maleic anhydride-derivative (A) and vinyl-derivative (B) pairings (See below.) allows the generation of a broad range of polymers, differing in repeat unit. These will be apparent to, and may be routinely generated by, a skilled person.

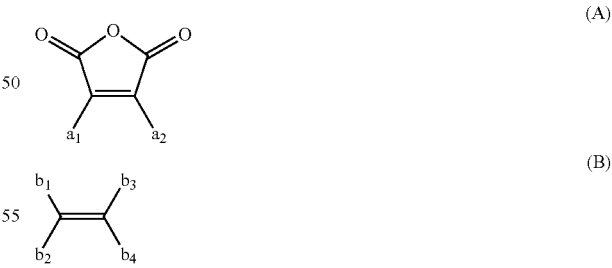

Chemical moieties $a_1$, $a_2$, $b_1$, $b_2$, $b_3$ and $b_4$ are not restricted, but at least one of $a_1$ and $a_2$ may be an electron-withdrawing species while at least one of $b_1$, $b_2$, $b_3$ and $b_4$ may be an electron-donating species, and vice versa (so as to stabilise the pre-polymer charge transfer complex between anhydride and alkene).

Suitable electron-withdrawing species $a_1$ and $a_2$ or $b_1$, $b_2$, $b_3$ and $b_4$ as appropriate include conjugated groups, including alka(poly)alkenyl and aryl (including $C_{6-10}$ aryl, preferably phenyl), alkoxyl (including $C_{1-24}$ alkoxyl), alkylthio (including $C_{1-24}$ alkylthio), alkanoyloxy (including $C_{1-6}$ alkanoyloxy) alkoxycarbonyl (including $C_{1-6}$ alkoxycarbonyl) and aryl (including $C_{6-10}$ aryl), all of which may be optionally substituted with an optionally electron-withdrawing substituent, such as fluoro, chloro, bromo, iodo and as appropriate nitro.

Suitable electron-donating species $b_1$, $b_2$, $b_3$ and $b_4$ or $a_1$ and $a_2$ as appropriate include alkyl (including $C_{1-6}$ alkyl which can have a linear or branched structure) and $C_{4-9}$ cycloalkyl.

Preferably, when $a_1$ is a proton, $a_2$ is a proton, methyl or phenyl substituent.

When $b_1$ and $b_2$ are protons, $b_3$ and $b_4$ are preferably methyl substituents.

When $b_1$, $b_2$ and $b_3$ are protons, $b_4$ preferably alkyl, aryl, alkoxyl (optionally substituted with an optionally electron-withdrawing substituent, such as fluoro, chloro, bromo, iodo and as appropriate nitro), or alkanoyloxyl. Preferably, $b_4$ is linear aliphatic, phenyl, or linear or branched alkoxyl (optionally substituted with hydroxyl or alkanoyloxyl) or alkanoyloxyl.

The maleic anhydride derivative (A) may be one substituted with an electron withdrawing substituent, while the vinyl derivative (B) may be one substituted with an electron donating substituent.

(A) is more preferably chosen from:
maleic anhydride; and
alkyl (including $C_{1-6}$ alkyl and $C_{4-9}$ cycloalkyl) substituted derivatives thereof, such as methyl maleic anhydride, and dimethyl maleic anhydride; and
aryl (including $C_{6-10}$ aryl) substituted derivatives thereof, such as phenyl maleic anhydride, and diphenyl maleic anhydride.

(B) is more preferably chosen from:
alkene (including $C_{1-24}$ alkene), such as ethylene, butylene, isobutylene and octadecene;
alkoxyl (including $C_{1-24}$ alkoxyl) substituted derivatives thereof, such as vinyl ethers, including methyl vinyl ether, ethyl vinyl ether, propyl vinyl ether, n-butyl vinyl ether, i-butyl vinyl ether, t-butyl vinyl ether, dodecyl vinyl ether, octadecyl vinyl ether and allylethyl ether; optionally substituted with an optionally electron-withdrawing substituent, such as hydroxyl or alkanoyloxyl, such as alkanediol vinyl ethers, including 1,2-ethanediol vinyl ether, 1,3-propanediol vinyl ether, 1,4-butanediol vinyl ether, 1,5-pentanediol vinyl ether, and hexanediol vinyl ether; and ester derivatives thereof;
alkanoyloxy (including $C_{1-6}$ alkanoyloxy) substituted derivatives thereof, such as vinyl acetate;
aryl (including $C_{6-10}$ aryl) substituted derivatives thereof, such as styrene, and substituted derivatives thereof, such as those substituted with methyl, fluoro, chloro, bromo, iodo and nitro.

The application of a chiral solvent, or chirally biased solvent of reaction, for example 1R,2S,5R-menthol, allows further variation in polymer structure compared to polymerisations in racemic or achiral solvents (Doiuchi, T., Minoura, Y. *Macromolecules*, 1978, 11, 270).

The polymers of the present invention are derivatives based on maleic anhydride-derived alternating copolymers that have been reacted at the anhydride moiety, in a percentage between 1% and 100% functionalisation, with a compound, or many compounds, containing a nucleophilic group. In a class of copolymers of the present invention the copolymer is reacted at the anhydride moiety, in a percentage between 1% and 100% functionalisation, with a compound, or many compounds, containing an alcohol, thiol, isocyanate or amine chemically functional group (Paleos, C. M., Tsiourvas, D., Anastassopoulou, J., Theophanides, T., *Polymer*, 1992, 33, 4047; McCormick, C. L., Chang, Y., *Macromolecules*, 1994, 27, 2151). Preferably it is an amine-derivatised chemically functional compound (R—$NH_2$). The extent and selectivity of the attached chemical function is determined by the nature of the adjacent substituent groups 1-4:

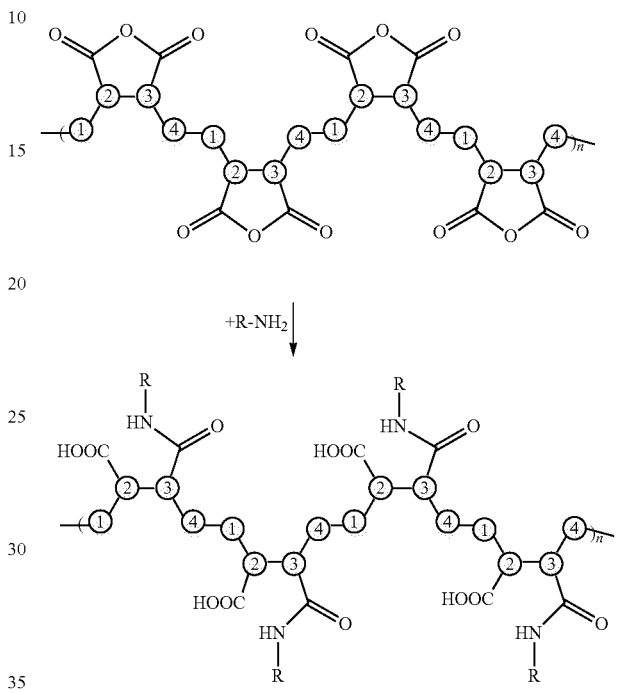

Thus, in a class of copolymers of the present invention there is provided a copolymer comprising residues of a maleic anhydride derivative and those of a compound containing vinylic unsaturation, and those of a compound containing an amine group.

The geometrical specificity of this functionalisation reaction can be enforced by the substituent groups of the polymeric anhydride, 1-4, and/or the amine substituent, R. For example, we discovered that the model reaction of phenylamine with benzoxysuccinic anhydride specifically afforded the amic acid isomer shown below:

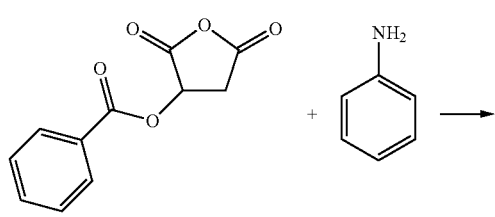

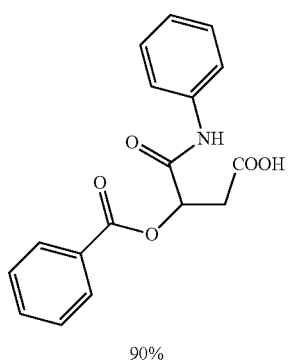

90%

Furthermore, the poly(amic acid) functional polymers so produced can be converted, by dehydration (chemically or by heating), to form the corresponding poly(imide):

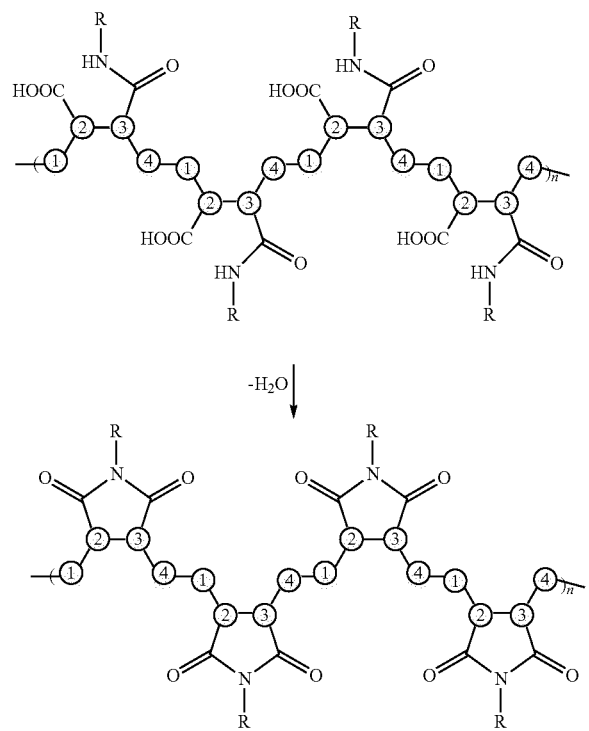

Thus, in another class of copolymers of the present invention there is provided a copolymer comprising residues of a compound containing vinylic unsaturation, and those of a compound containing an amine group, characterised in that it comprises residues of a maleimide derivative.

That is, a maleic anhydride derivative, in which both carboxylic functions of the anhydride moiety have been reacted with an isocyanate or amine chemically functional group.

Surprisingly, it was noted that nucleophilic R derivatives, particularly tertiary amines, of these poly(imide)s based upon vinyl ethers were strongly coloured polymers (see Examples 28-29 and also Simms, J. A., Corcoran, P. H., *Progress in Organic Coatings*, 1995, 26, 217.). Further experiments revealed that the essential component for colour was the terminal structural motif:

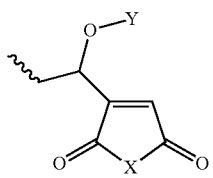

X = O, NH, NR
Y = any possible

If R was not basic, a nucleophile such as triethylamine could be added in a suitable solvent to generate colour (dimethylformamide was also suitably nucleophilic). The coloured phenomenon was a useful indicator of conversion of poly(amic acid) to poly(imide). The poly(imide)s are predictably acid and base sensitive and are rapidly converted back to the corresponding poly(amic acid)s by 1 M HCl for example.

The functionalised poly(anhydride)s described above, poly(amic acid)s and poly(imide)s can be prepared as materials soluble or insoluble in water or other water based fluids, such as serum or saline solution. The extent and rate of solubility can be tailored by applying the appropriate poly(anhydride) chemistry and/or molecular weight.

The copolymers of the present invention have a wide range of activities, including the sequestration of atomic, ionic or molecular species for the purpose of, for example, radical or oxidant elimination, metal ion sequestration, peptide or protein or enzyme binding or disulfide bridge formation.

In one class of the copolymers, those that have been reacted at the anhydride moiety with an amine-derivatised chemically functional compound R—NH$_2$, R—NH$_2$ is preferably a chemically or physiologically functional molecule; and more preferably a chemically functional molecule capable of the sequestration of atomic, ionic or molecular species for the purpose of, for example, radical or oxidant elimination, metal ion sequestration, peptide or protein or enzyme binding or disulfide bridge formation.

The copolymers of the present invention, however, do not only sequester or bind undesirable species.

The polymers may be produced by the attachment of functional compounds to alternating copolymers of maleic anhydride derivatives and vinyl derivatives, with optional subsequent dehydration (chemically or by heating) to form other copolymers of the present invention. The incorporation of actives on these polymers can confer unexpected advantageous properties: for example, enhanced activity, enhanced lifetime and/or enhanced specificity of interaction with the biochemical environment, and/or decreased cytotoxicity. These chemical and biological properties of the conjugated active can be rapidly modified applying structural variants to the polymers.

For example, the activity of inhibitors of proteases and other small molecule active drugs may be enhanced by the polymers. Specifically, the polymers enhance the inhibitory activity of a serine protease inhibitor.

The lifetime of unstable drugs may be enhanced by the polymers. Specifically, the polymers enhance the lifetime of a neurotransmitter drug, such as dopamine, and a serine protease inhibitor, such as 4-(2-aminoethyl)-benzene sulphonyl fluoride (AEBSF, PefaBloc).

Cytotoxicity is one of the chemical and biological properties that can be readily modified applying structural variants of the present polymers. Specifically, the polymers reduce the cytotoxicity of a serine protease inhibitor, such as 4-(2-aminoethyl)-benzene sulphonyl fluoride (AEBSF, PefaBloc).

The present polymers may also be designed to bind to specific extracellular matrix species, producing discrete complexes from aqueous media. In this manner, the invention allows the geometrically specific presentation of biomolecules, at the molecular level, on a polymer, leading to enhanced specificity of interaction with the biochemical environment.

These biomolecules may be proteins (including enzymes, antibodies or antibody fragments), peptides (including growth factors or cytokines), deoxyribonucleic oligomers and chains (including whole or partial genes) or polysaccharides (including heparin, heparan sulphate, laminin, chondroitin sulphate, dermatan sulphate, keratan sulphate or hyaluronate) or fusions of any of the aforementioned moieties, for example fusion peptides of heparin and a peptide sequence.

The polymeric nature of these materials can be exploited to confer the expected variation in physical properties observed for other polymers.

The molecular weight of these polymers can be selected to exploit localisation advantages.

For example, the solubility of the material can be varied independently of the attached functional group, and can be tuned to allow an active compound containing a nucleophilic group that is soluble in water or other water based fluids, such as serum or saline solution, to be incorporated in a copolymer of the present invention that is insoluble in water, or extent and rate of solubility of which can be tailored by applying the appropriate poly(anhydride) chemistry and/or molecular weight.

This advantageously enables an otherwise systemic therapy to be localised inside or outside of the body, including in devices, preferably medical devices in the form of films, foams, coatings, fibres or monoliths suitable for management of the body outide the body. Such devices include articles for the in situ purification of bodily fluids, such as blood and/or wound exudate outide the body. Such devices include ultrafiltration artefacts, including coatings and membranes used for ex situ purification of bodily fluids.

The molecular weight of these polymers can be selected to exploit localisation advantages in other ways, for example, by localisation behind a biological or synthetic barrier. The blood-brain barrier, cancerous growths, the vascular and lymphatic systems all offer barriers segregating molecular weight and chemical characteristics.

Active macromolecules can be localised inside or outside of such biological barriers.

Dialysis membranes offer a synthetic system for the localisation of high molecular weight actives.

These membranes can be fabricated into devices for internal and external medical applications, for example at the site of a wound, bone fracture, surgical incision or other soft-tissue lesion (including cartilage and ligament defects or damage) or in spinal repair.

The polymeric nature of these materials also allows the manufacture of three-dimensional devices for cell attachment and directed cell movement. These devices can be made permanent or bioresorbable. We provide a biologically appropriate technology that allows the facility for non-contact specific alteration of structure and specific interactions at the molecular level. Laser heating allows the designation of surface characteristics on the micrometer scale. For example, areas allowing or disallowing cell attachment can be designated. In addition, molecular circuitry can be designated in this manner for applications such as computation or diagnostics. The polymers can be applied to produce devices that, when swollen with aqueous fluids, take on a final shape dictated by the surface, or internally created design (in two or three dimensions). For example, a surface design may be created by laser to create chemical modifications. When immersed in an aqueous fluid, differential expansion by fluid uptake is constrained by the laser design and a mechanically predicted conformation is the result. This technology can be developed to create many varied final device shapes.

When the active compound containing a nucleophilic group (the residues of which are comprised in the copolymer) is a compound of formula R—$NH_2$, suitable R—$NH_2$ actives for incorporation into these polymers include:

antibiotics, including antibacterials, such as aminoguanidine, and antifungals, such as Amphotericin B; and neurotransmitters, such as 3-hydroxytyramine (dopamine) and serotonin;

They also include anion or cation chelators, including metal ion chelators and metal ion-sequestering agents, such as transition metal ion chelators, such as desferrioxamine (DFO), 3-hydroxytyramine (dopamine), 2-aminoethanethiol, 2-aminopropionitrile, 3-aminopropionitrile, N-(3'-aminopropyl)-2-pyrrolidinone, N-(3-aminopropyl)-morpholine, 2-(2-aminoethyl)-pyridine, 1-(3-aminopropyl)imidazole, N-(2-aminoethyl)pyrrolidine, 2-(2-aminoethyl)-5-nitropyridine, N-(3'-aminopropyl)-pyrrolidinone; sodium, potassium or calcium ion chelators, such as crownethers, such as aza-18-crown-6-ether and aza-15-crown-5-ether;

They further include moieties specifically recognised by proteins in the coagulation cascade; protease inhibitors, such as serine protease inhibitors, such as 4-(2-aminoethyl)-benzene sulphonyl fluoride (AEBSF, PefaBloc) and Nα-p-tosyl-L-lysine chloromethyl ketone (TLCK) and ε-aminocaproyl-p-chlorobenzylamide;

cysteine protease inhibitors; matrix metalloprotease inhibitors; and carboxyl (acid) protease inhibitors; and anti-oxidants, such as 3-hydroxytyramine (dopamine);

They also include functional compounds specifically recognised by proteins or polysaccharides, such as functional compounds comprising a group recognised by glycosaminoglycans (including heparin, heparan sulphate, laminin, chondroitin sulphate, dermatan sulphate, keratan sulphate or hyaluronate) such as imidazole species such as histamine or 1-(3-aminopropyl)imidazole, optionally non-covalently combined with a glycosaminoglycan, such as heparin, heparan sulphate, laminin, chondroitin sulphate, dermatan sulphate, keratan sulphate or hyaluronate to give materials designed to regulate biochemical processes.

They include fluorophors, such as 5-(2-aminoethylamino)-1-naphthalene sulphonic acid, sodium salt lumophors, such as N-(4-aminobutyl)-N-ethyl-isoluminol; and calmodulin antagonists, such as N-(4-aminobutyl)-2-naphthalenesulfonamide and N-(4-aminobutyl)-5-chloro-1-naphthalenesulfonamide; and calmodulin/$Ca^{2+}$ activated phosphodiesterase inhibitors, such as N-(4-aminobutyl)-5-chloro-2-naphthalenesulfonamide They also include $GABA_B$ receptor ligands, such as 4-aminobutylphosphonic acid ε-aminocaproyl-β-D-galactopyranosylamine sugars peptides (including growth factors or cytokines, e.g. bacterial cytokines, such as α-amino-γ-butyrolactone and L-homocarnosine);

deoxyribonucleic oligomers and chains (including whole or partial genes) or sacrificial materials, such as N-α-carbobenzyloxy-L-lysine 4-nitrophenyl ester hydrochloride (side chain cleavable by cathepsin B and plasmin); and NO generators, such as 3-(aminopropyl)-1-hydroxy-3-isopropyl-2-oxo-1-triazene (NOC-5).

In a second aspect, the present invention also provides artefacts formed from the functional materials of the invention as described herein. Such artefacts include solid structural devices, preferably medical devices in the form of films, foams, coatings, fibres or monoliths suitable for management of the local biological environment, internal or external.

Such artefacts also include articles for the in situ purification of water, including antibacterial and desalinating coatings.

Such artefacts also include solid and fluid artefacts. They may be incorporated in medicinal delivery means, such as conventional topical means, e.g. dressings, bandages and other wound coverings. Such artefacts also include compositions, such as medicinal compositions suitable for management of the wound environment, in situ or ex situ.

Such compositions may be in the form of conventional fluid medicinal delivery means, comprising conventional aqueous and non-aqueous diluents, excipients and vehicles.

These include particulates, including granulates and powders, creams, gels, ointments and salves, and dispersions, emulsions, suspensions and solutions.

Such compositions also include medicinal compositions for management of the wound environment and/or bodily fluids ex situ, such as in dialysis.

In a third aspect, the present invention provides a method of using the copolymers of the first aspect of the present invention or the artefacts of the second aspect of the present invention, in particular a method of therapy or prophylaxis, inside or outside of the body.

In one embodiment of this third aspect of the present invention there is provided a method for the in situ purification of water, including antibacterial and desalinating activity.

In another embodiment there is provided a method for the treatment or prophylaxis of wounds, characterised in that it comprises administering a therapeutically effective amount of a polymer of the first aspect of the present invention or a solid device, dressing or scaffold or a fluid adhesive or medicinal composition of the second aspect of the present invention to a patient.

In one form thereof, there is provided a method for the treatment or prophylaxis of oxidative stress in a wound characterised in that it comprises administering a therapeutically effective amount of a metal ion chelator and/or metal ion-sequestering agent, a protease inhibitor, an anti-oxidant, a functional compound comprising a group recognised by glycosaminoglycans (GAGs), optionally combined with a glycosaminoglycan, such as heparin, and/or a peptide or protein or fusion peptide or enzyme binder in a copolymer of the first aspect of the present invention or an artefact of the second aspect of the present invention.

In one embodiment of the present invention there is provided a method for the in situ purification of water, including antibacterial and desalinating activity.

In another embodiment of this aspect of the present invention there is provided in particular a method of therapy or prophylaxis, effected outside of the body. Examples include methods of using preferably medical devices in the form of films, foams, coatings, fibres or monoliths suitable for management of the body outide the body. Such devices include articles for the in situ purification of bodily fluids, such as blood and/or wound exudate outide the body. Such devices include ultrafiltration artefacts, including coatings and membranes used for ex situ purification of bodily fluids.

BRIEF DESCRIPTION OF DRAWINGS

FIG. 1 shows the inhibitory performance of a serine protease inhibitor and its conjugate with copolymer assessed against serine proteases;

FIG. 2 shows the results of assaying respective protease inhibition activities with ageing time for a serine protease inhibitor and its conjugate with copolymer;

FIG. 3 shows cytotoxicity of a serine protease inhibitor and its conjugate with copolymer assessed in vitro on a culture of P3 chondrocytes;

FIG. 4 shows an elastase inhibition assay for a conjugate of a serine protease inhibitor with copolymer;

FIG. 5 shows the aqueous solution lifetime of dopamine compared to conjugates with copolymer by their rate of auto-oxidation;

FIG. 6 shows upheld activity of catechol active moiety in a copolymer conjugate by means of a UV-vis titration;

FIG. 7 shows an image of the complex of active heparin with copolymer as an elastic phase separated mass;

FIG. 8 shows an image of the complex of a polymeric fluorescent reporting moiety with copolymer with shifted emission wavelength;

FIG. 9 shows cell attachment to copolymers;

FIG. 10 shows laser designated patterning of copolymer discs having cell attachment in designated areas only;

FIG. 11 shows a fluorescent copolymer conjugate contained inside a dialysis button;

FIG. 12 shows the dialysis button of FIG. 11 demonstrating dialysis in a static environment;

FIG. 13 shows an image of a highly porous plug of copolymer for tissue engineering applications;

FIG. 14 shows the plug of FIG. 13 as a scaffold seeded with fibroblasts;

FIG. 15 shows an image of a self-forming copolymer device which has been laser patterned and swollen;

DETAILED DESCRIPTION

Figure 16:
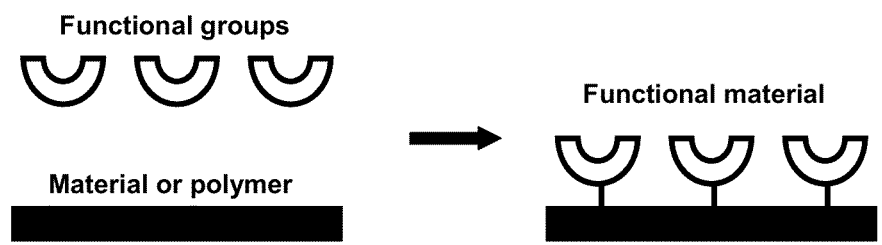
FIG. 16 is a diagram which shows chemically functional appendages covalently bonded in accordance with the present invention.
Figure 17:
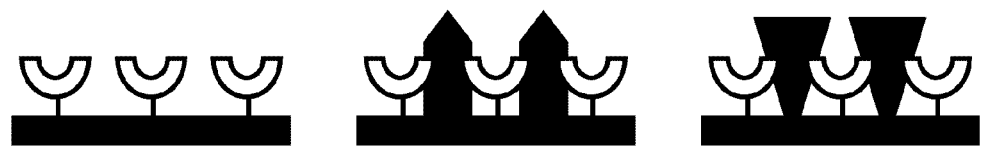
FIG. 17 is a schematic representation of an immediate surrounding polymer structure in accordance with the present invention.
Figure 18:
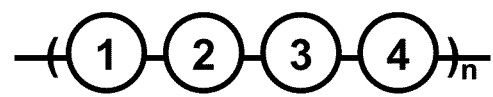
FIG. 18 is an illustration of four adjacent and regularly repeating sites in a selected polymer system in accordance with the present invention.

The invention will now be further described with reference to the following Examples, in which:

Examples 1-41 exemplify methods for the preparation of the functionalised copolymers of the present invention by the attachment of functional compounds to alternating copolymers of maleic anhydride derivatives and vinyl derivatives.

Examples 42-44 demonstrate the activity of some of the copolymers of Examples 1-41, and the unexpected advantages of the copolymers when compared with the unattached functional compounds.

Examples 45-50 demonstrate the unexpected and advantageous applications of some of the copolymers of Examples 1-41.

EXAMPLE 1

Aza-18-crown-6 Derivatisation of maleic anhydride-alt-ethylene copolymer

Maleic anhydride-alt-ethylene copolymer (0.120 g, 0.95 mmol unit) was dissolved in DMF (3 ml) and heated to 100°

C. To this stirred solution, a solution of aza-18-crown-6 (0.250 g, 0.95 mmol) in DMF (3 ml) was added dropwise. Heating at 100° C. was continued for 1 hour. The reaction mixture was allowed to cool to room temperature and stirring was continued for a further 4 hours.

The reaction mixture was added dropwise to toluene (100 ml), causing the precipitation of a swollen gel, which was removed, and rotary evaporated to dryness. The brittle product so produced was stored in the absence of air. Yield 0.351 g, 95%.

EXAMPLE 2

Aza-15-crown-5 Derivatisation of maleic anhydride-alt-isobutylene copolymer

Maleic anhydride-alt-ethylene copolymer (0.288 g, 2.28 mmol unit) was dissolved in DMF (5 ml) and heated to 100° C. To this stirred solution, a solution of aza-15-crown-5 (0.500 g, 2.28 mmol) in DMF (3 ml) was added dropwise. Heating at 100° C. was continued for 1 hour. The reaction mixture was allowed to cool to room temperature and stirring continued for a further 4 hours. The reaction mixture was added dropwise to toluene (100 ml), causing the precipitation of a swollen gel, which was removed, and rotary evaporated to dryness. The brittle product so produced was stored in the absence of air. Yield 0.724 g, 92%.

EXAMPLE 3

Desferrioxamine Derivatisation of maleic anhydride-alt-isobutylene copolymer

Maleic anhydride-alt-isobutylene copolymer (0.579 g, 3.8 mmol unit) was dissolved in DMF (50 ml). To this stirred solution, a solution of desferrioxamine mesitylate (2.467 g, 3.8 mmol) and triethylamine (0.380 g, 3.8 mmol) in DMF (50 ml) was added dropwise. Stirring was continued for 12 hours. The reaction mixture was poured into 1M HCl (500 ml) to precipitate a yellow viscoelastic product, which was removed, rotary evaporated to dryness and dried in a vacuum desiccator overnight. Yield 1.268 g, 47%.

EXAMPLE 4

Deferrioxamine Derivatisation of maleic anhydride-alt-methyl vinyl ether copolymer Maleic anhydride-alt-methylvinylether copolymer (0.198 g, 1.3 mmol unit) was dissolved in DMF (15 ml). To this stirred solution, a solution of desferrioxamine mesitylate (0.833 g, 1.3 mmol) and triethylamine (0.128 g, 1.3 mmol) in DMF (20 ml) was added dropwise.

Stirring was continued for a further 2 hours. The reaction mixture was poured into 1M HCl (500 ml) to precipitate a white viscoelastic product, which was removed, rotary evaporated to dryness and dried in a vacuum desiccator overnight. Yield 0.399 g, 44%.

EXAMPLE 5

Deferrioxamine Derivatisation of maleic anhydride-alt-styrene copolymer

Maleic anhydride-alt-styrene copolymer (0.420 g, 2.1 mmol unit) was dissolved in DMF (15 ml). To this stirred solution, a solution of desferrioxamine mesitylate (1.364 g, 2.1 mmol) and triethylamine (0.210 g, 2.1 mmol) in DMF (20 ml) was added dropwise. Stirring was continued for a further 2 hours. The reaction mixture was poured into 1M HCl (500 ml) to precipitate a white viscoelastic product, which was removed, rotary evaporated to dryness and dried in a vacuum desiccator overnight. Yield 1.002 g, 63%.

EXAMPLE 6

3-hydroxytyramine Derivatisation of maleic anhydride-alt-methyl vinyl ether copolymer Maleic anhydride-alt-methylvinylether copolymer (1.462 g, 9.4 mmol unit) was dissolved in DMF (60 ml) and heated to 100° C. A solution of 3-hydroxytyramine (1.775 g, 9.4 mmol) and triethylamine (0.947 g, 9.4 mmol) in DMF (10 ml) was added slowly. Heating at 100° C. was continued for 35 min. The reaction mixture was allowed to cool to room temperature. The reaction mixture was poured onto 1M HCl (700 ml) to precipitate the product, which was filtered and washed with 1M HCl (50 ml), dried by suction and dried in a vacuum desiccator overnight. The white powder, yield 0.286 g, 29%. $NaIO_4$ test turned the product brown indicating attachment of the dopamine.

$^1$H-NMR (270 MHz, $d_7$-DMF, ppm): 7.67 (br, Ar); 7.11 (br, Ar(phenyl)); 6.75 (br, Ar(dopamine)); 6.54 (br, Ar(dopamine); 6.34 (br, 1H, Ar(phenyl)); 3.30-2.60 (br, 3H, CH); 2.61 (br, 4H, $CH_2$(dopamine)); 2.28-1.33 (br, 2H, $CH_2$ (backbone)).

EXAMPLE 7

3-hydroxytyramine Derivatisation of chiral maleic anhydride-alt-styrene copolymer Maleic anhydride-alt-styrene copolymer (chiral) (2.06 g, 10.0 mmol unit) was dissolved in DMF (50 ml) and heated to 100° C. A solution of 3-hydroxytyramine (1.93 g, 10.0 mmol) and triethylamine (1.03 g, 10.0 mmol) in DMF (20 ml) was added slowly. Heating at 100° C. was continued for 35 min. The reaction mixture was allowed to cool to room temperature. The reaction mixture was poured onto 1M HCl (700 ml) to precipitate the product, which was filtered and washed with 1M HCl (50 ml), dried by suction and dried in a vacuum desiccator overnight. The white powder, yield 3.590 g, 100%. $NaIO_4$ test turned the product brown indicating attachment of the dopamine.

$^1$H-NMR (270 MHz, $d_7$-DMF, ppm): 7.12 (br, Ar(phenyl)); 6.75 (br, Ar(dopamine)); 6.48 (br, Ar(dopamine); 6.30-5.50 (br, Ar); 3.30-2.60 (br, 3H, CH); 2.61 (br, 4H, $CH_2$(dopamine)); 2.28-1.33 (br, 2H, $CH_2$(backbone)).

EXAMPLE 8

3-hydroxytyramine Derivatisation of maleic anhydride-alt-styrene copolymer

Maleic anhydride-alt-styrene copolymer (2.00 g, 9.89 mmol unit) was dissolved in DMF (50 ml) and heated to 100° C. A solution of 3-hydroxytyramine.HCl (1.88 g, 9.89 mmol) and triethylamine (1.00 g, 9.89 mmol) in DMF (20 ml) was added slowly. Heating at 100° C. was continued for 1 hour. The reaction mixture was allowed to cool to room temperature and stirring continued for 2 hours. The reaction mixture was poured onto 1M HCl (500 ml) to precipitate the product, which was filtered and washed with 1M HCl (50 ml), dried by suction and dried in a vacuum desiccator overnight. The white powder, yield 3.085 g, 80%. NaIO$_4$ test turned the product brown indicating attachment of 3-hydroxytyramine.

$^1$H-NMR (270 MHz, d$_7$-DMF, ppm): 7.12 (br, 4H, Ar(phenyl)); 6.74 (br, 2H, Ar(3-hydroxytyramine)); 6.54 (br, 1H, Ar(3-hydroxytyramine); 6.34 (br, 1H, Ar(phenyl)); 3.30-2.60 (br, 3H, CH); 2.61 (br, 4H, CH$_2$(3-hydroxytyramine)); 2.28-1.33 (br, 2H, CH$_2$(backbone)).

EXAMPLE 9

3-hydroxytyramine Derivatisation of maleic anhydride-alt-n-butylvinylether copolymer Maleic anhydride-alt-n-butylvinylether copolymer (2.00 g, 10.0 mmol unit) was dissolved in DMF (50 ml) and heated to 100° C., at which point the solution started to turn pink. A solution of 3-hydroxytyramine.HCl (1.91 g, 10 mmol) and triethylamine (1.01 g 10 mmol) in DMF (20 ml) was added slowly. During this addition, the solution became very dark purple in colour. Heating at 100° C. was continued for 45 min. The reaction mixture was allowed to cool to room temperature and stirring continued for 2 hours. The reaction mixture was poured onto 1M HCl (600 ml) to precipitate the product, which was filtered, washed with 1M HCl (50 ml), dried by suction and dried in a vacuum desiccator overnight. Yield 2.698 g, 76%. NaIO$_4$ test turned the product brown indicating attachment of the 3-hydroxytyramine.

IR (cast film, KBr disc)/cm$^{-1}$: 3319; 2958, 2934, 2873; 1703; 1648; 1604; 1523; 1444; 1363; 1283; 1196; 1114.

$^1$H-NMR (270 MHz, d$_7$-DMF ppm): 6.74 (br, 2H, Ar); 6.53 (br, 1H, Ar); 4.96 (br, 1H, NH); 3.38 (br, 5H, CHO—, CH$_2$O—, CH); 2.67 (br, 4H, CH$_2$(3-hydroxytyramine)); 2.00 (br, 2H, CH$_2$(backbone)); 1.51 (br, 2H, CH$_2$(butyl chain)); 1.33 (br, 2H, CH$_2$(butyl chain)); 0.87 (br, 3H, CH$_3$). $^1$H-NMR integration indicated that the polymer was 95-100% functionalised with 3-hydroxytyramine.

EXAMPLE 10

3-hydroxytyramine Derivatisation of maleic anhydride-alt-isobutylene copolymer Maleic anhydride-alt-isobutylene copolymer (2.00 g, 13.0 mmol unit) was dissolved in DMF (50 ml) and heated to 100° C. A solution of 3-hydroxytyramine.HCl (2.46 g, 13 mmol) and triethylamine (1.31 g 13 mmol) in DMF (20 ml) was added slowly. Heating at 100° C. was continued for 1 hour. The reaction mixture was allowed to cool to room temperature and stirring continued for 2 hours. The reaction mixture was poured onto 1M HCl (1000 ml) to precipitate the product, which was filtered, washed with 1M HCl (50 ml), dried by suction and dried in a vacuum desiccator overnight.

Yield 2.698 g, 60%. NaIO$_4$ test turned the product brown indicating attachment of the 3-hydroxytyramine.

IR (cast film, KBr disc)/cm$^{-1}$: 3270; 2968; 1708; 1585; 1528; 1447; 1373; 1284; 1248; 1197; 1116; 1056.

$^1$H-NMR (270 MHz, d$_7$-DMF, ppm): 9.13 (br, 1H, OH); 6.75 (br, 2H, Ar); 6.55 (br, 1H, Ar); 3.44 (br, 2H, CH); 2.74 (br, 2H, CH$_2$(3-hydroxytyramine)); 1.96 (br, 2H, CH$_2$(3-hydroxytyramine)); 1.33 (br, 2H, CH$_2$(backbone)); 1.08 (br, 6H, CH$_3$).

EXAMPLE 11

3-hydroxytyramine Derivatisation of maleic anhydride-alt-ethylene copolymer Maleic anhydride-alt-ethylene copolymer (2.00 g, 16.0 mmol unit) was dissolved in DMF (50 ml) and heated to 100° C. A solution of 3-hydroxytyramine.HCl (3.01 g, 16 mmol) and triethylamine (1.60 g 16 mmol) in DMF (20 ml) was added slowly. Heating at 100° C. was continued for 1 hour. The reaction mixture was allowed to cool to room temperature and stirring continued for 2 hours. The reaction mixture was poured onto toluene (600 ml) to precipitate the product, which was dried by evaporation under reduced pressure, washed with 1M HCl (~300 ml) and dried in a vacuum desiccator overnight. Yield 2.591 g, 52%. NaIO$_4$ test turned the product brown indicating attachment of the 3-hydroxytyramine.

$^1$H-NMR (270 MHz, d$_6$-pyridine, ppm): 9.25 (br, 1H, OH); 8.29 (br, 2H); 7.89 (br, 2H); 7.22 (br, 2H, Ar); 6.75 (br, 1H, Ar); 3.74 (br, 2H, CH); 3.00 (br, 4H, CH$_2$(3-hydroxytyramine)); 2.23 (br, 4H, CH$_2$(backbone)).

EXAMPLE 12

3-hydroxytyramine Derivatisation of maleic anhydride-alt-n-octadecylvinylether copolymer Maleic anhydride-alt-octadecylvinylether copolymer (2.00 g, 5.07 mmol unit) was dissolved in DMF (50 ml) and heated to 100° C. until the polymer had dissolved/melted. Triethylamine (1.31 g 13 mmol) was added and the solution turned purple. A solution of 3-hydroxytyramine.HCl (2.46 g, 13 mmol) in DMF (20 ml) was added slowly. Heating at 100° C. was continued for 1 hour. The reaction mixture was allowed to cool to room temperature and stirring continued for 2 hours.

The reaction mixture was poured onto 1M HCl (700 ml) to precipitate the product, which was filtered, washed with 1M HCl (50 ml) and acetone (50 ml), dried by suction. The product was further dried by evaporation under reduced pressure with strong heating followed by storing in a vacuum desiccator overnight. Yield 0.389 g, 13%. NaIO$_4$ test turned the product brown indicating attachment of the 3-hydroxytyramine.

IR (cast film, KBr disc)/cm$^{-1}$: 3339; 2926, 2852; 1775; 1697; 1650; 1606; 1526; 1446; 1358; 1284; 1196; 1112.

$^1$H-NMR (270 MHz, d$_7$-DMF, ppm): 6.74 (br, 2H, Ar); 6.52 (br, 1H, Ar); 3.80-2.5 (br, 9H, CH, CH$_2$(backbone)); 1.31 (br, 34H, CH$_2$(alkyl chain)); 0.91 (br, 3H, CH$_3$).

EXAMPLE 13

3-hydroxytyramine Derivatisation of maleic anhydride-alt-octadecene copolymer Maleic anhydride-alt-octadecene copolymer (2.00 g, 5.71 mmol unit) was dissolved in DMF (50 ml) and heated to 100° C. Triethylamine (0.577 g, 5.71 mmol) was added and a solution of 3-hydroxytyramine.HCl (1.08 g, 5.71 mmol) in DMF (20 ml) was added. The mixture was heated at 100° C. for 30 min and then cooled to room temperature. The mixture was poured onto 1M HCl (2×800 ml) to precipitate the product. The product was filtered, washed with 1M HCl, dried by suction and further dried overnight in a vacuum desiccator. Yield 2.045 g, 66%. NaIO$_4$ test turned the product brown indicating attachment of the 3-hydroxytyramine.

IR (cast film, KBr disc)/cm$^{-1}$: 3300; 2923, 2852; 1776; 1710; 1605; 1527; 1454; 1360; 1283; 1196; 1114.

$^1$H-NMR (270 MHz, d$_7$-DMF, ppm): 6.74 (br, 2H, Ar); 6.56 (br, 1H, Ar); 3.41 (br, 2H, CH); 2.71 (br, 7H, CH$_2$, CH(octadecene)); 1.29 (br, 30H, CH$_2$(octadecene)); 0.89 (br, 3H, CH$_3$(octadecene)).

EXAMPLE 14

4-(2-aminoethyl)benzenesulphonylfluoride Derivatisation of maleic anhydride-alt-isobutylene copolymer

Maleic anhydride-alt-isobutylene copolymer (0.643 g, 2.09 mmol unit) was dissolved in DMF (25 ml) at room temperature.

A solution of 4-(2-aminoethyl)benzenesulphonylfluoride (0.500 g, 2.09 mmol) and triethylamine (0.211 g, 2.09 mmol) in DMF (10 ml) was added dropwise. The solution was stirred for 90 minutes at room temperature. The mixture was poured into 0.5 M HCl (250 ml) to precipitate the white product. The product was filtered, washed with distilled water, dried by suction and further dried overnight in a vacuum desiccator. Yield 1.062 g, 100%. Storage at <0° C. IR (cast film, KBr disc)/cm$^{-1}$: Amide; 1705, 1593.

$^1$H-NMR (270 MHz, d$_6$-acetone, ppm): 8.00 (br, 2H, Ar); 7.60 (br, 2H, Ar); 3.70 (br, 2H, CH); 2.70 (br, 2H, CH$_2$); 2.60 (br, 4H, CH$_2$(AEBSF)); 1.00 (br, 6H, CH$_3$).

$^{19}$F-NMR (270 MHz, d$_6$-acetone, ppm): 66.21 (br). Elemental Analysis: C, 52.33%; H, 6.00%; N, 4.53%; F 4.19% (ambient temperature transit).

EXAMPLE 15

4-(2-aminoethyl)benzenesulphonylfluoride Derivatisation of maleic anhydride-alt-octadecene copolymer

Maleic anhydride-alt-octadecene copolymer (0.713 g, 2.09 mmol unit) was dissolved in DMF (25 ml) at room temperature. A solution of 4-(2-aminoethyl)benzenesulphonylfluoride (0.500 g, 2.09 mmol) and triethylamine (0.211 g, 2.09 mmol) in DMF (10 ml) was added dropwise. The solution was stirred for 90 minutes at room temperature. The mixture was poured into 0.5 M HCl (250 ml) to precipitate the white product. The product was filtered, washed with distilled water, dried by suction and further dried overnight in a vacuum desiccator. Yield 0.863 g, 75%. Storage at <0° C. IR (cast film, KBr disc)/cm$^{-1}$: Amide; 1705, 1593.

$^1$H-NMR (270 MHz, d$_6$-acetone, ppm): 8.00 (br, 2H, Ar); 7.65 (br, 2H, Ar); 3.70 (br, 2H, CH); 3.00 (br, 2H, CH$_2$); 1.30 (br, 30H, CH$_2$); 0.90 (br, 3H, CH$_3$). $^{19}$F-NMR (270 MHz, d$_6$-acetone, ppm): 66.33 (br).

EXAMPLE 16

4-(2-aminoethyl)benzenesulphonylfluoride Derivatisation of maleic anhydride-alt-n-butylvinylether copolymer

Maleic anhydride-alt-n-butylvinylether copolymer (0.326 g, 2.09 mmol unit) was dissolved in DMF (25 ml) at room temperature. A solution of 4-(2-aminoethyl)benzenesulphonylfluoride (0.500 g, 2.09 mmol) and triethylamine (0.211 g, 2.09 mmol) in DMF (10 ml) was added dropwise. The solution was stirred for 90 minutes at room temperature.

The mixture was poured into 0.5 M HCl (250 ml) to precipitate the white product. The product was filtered, washed with distilled water, dried by suction and further dried overnight in a vacuum desiccator. Yield 0.374 g, 50%. Storage at <0° C. IR (cast film, KBr disc)/cm$^{-1}$: Amide; 1720, 1655.

$^1$H-NMR (270 MHz, d$_6$-acetone, ppm): 8.00 (br, 2H, Ar); 7.60 (br, 2H, Ar); 5.00-2.00 (multiple conformational, 15H); 1.70 (br, 3H, CH$_3$). $^{19}$F-NMR (270 MHz, d$_6$-acetone, ppm): 66.18 (br).

EXAMPLE 17

4-(2-aminoethyl)benzenesulphonylfluoride Derivatisation of maleic anhydride-alt-styrene copolymer

Maleic anhydride-alt-styrene copolymer (0.422 g, 2.09 mmol unit) was dissolved in DMF (25 ml) at room temperature. A solution of 4-(2-aminoethyl)benzenesulphonylfluoride (0.500 g, 2.09 mmol) and triethylamine (0.211 g, 2.09 mmol) in DMF (10 ml) was added dropwise. The solution was stirred for 90 minutes at room temperature. The mixture was poured into 0.5 M HCl (250 ml) to precipitate the white product. The product was filtered, washed with distilled water, dried by suction and further dried overnight in a vacuum desiccator. Yield 0.775 g, 92%. Storage at <0° C. IR (cast film, KBr disc)/cm$^{-1}$: Amide; 1705, 1593.

$^1$H-NMR (270 MHz, d$_6$-acetone, ppm): 8.00 (br, 2H, Ar); 7.60 (br, 2H, Ar); 7.10 (br, 5H, Ar); 3.70-1.5 (multiple conformational, 9H). $^{19}$F-NMR (270 MHz, d$_6$-acetone, ppm): 66.19 (br).

EXAMPLE 18

4-(2-aminoethyl)benzenesulphonylfluoride Derivatisation of maleic anhydride-alt-methyl vinyl ether copolymer

Maleic anhydride-alt-methylvinylether copolymer (1.070 g, 6.9 mmol unit) was dissolved in DMF (60 ml) at room temperature. A solution of 4-(2-aminoethyl)benzenesulphonylfluoride (1.642 g, 6.9 mmol) and triethylamine (0.693 g, 6.9 mmol) in DMF (15 ml) was added dropwise. The solution was stirred for 90 minutes at room temperature. The mixture was poured into 0.5 M HCl (1600 ml) to precipitate the white product. The product was filtered, washed with distilled water, dried by suction and further dried overnight in a vacuum desiccator. Yield 0.863 g, 75%. Storage at <0° C. IR (cast film, KBr disc)/cm$^{-1}$: Amide; 1705, 1593.

$^1$H-NMR (270 MHz, d$_7$-DMF, ppm): 8.15 (br, 2H, Ar); 7.75 (br, 2H, Ar); 4.00-3.00 (multiple conformational, 9H); 2.00 (br, 3H, CH$_3$). $^{19}$F-NMR (270 MHz, d$_7$-DMF, ppm): 66.89 (br).

EXAMPLE 19

Histamine Derivatisation of maleic anhydride-alt-ethylene copolymer

Maleic anhydride-alt-ethylene copolymer (1.636 g, 13 mmol unit) was dissolved in DMF (60 ml) at ambient temperature. A solution of histamine (1.441 g, 13 mmol) in DMF (15 ml) was added dropwise at ambient temperature. The solution was left to stand for 1 h, during which time gelation occurred. The gel was rotary evaporated to dryness to produce a homogeneous white powder. Yield 3.08 g, 100%. IR (cast film, KBr disc)/cm$^{-1}$: Amide; 1650, 1548.

$^1$H-NMR (270 MHz, d$_7$-DMF, ppm): 8.50 (1H, Ar); 7.15 (1H, Ar); 3.40 (br, 2H, CH); 2.70 (br, 2H, CH$_2$); 2.35 (br, 2H, CH$_2$); 1.35 (br, 4H, CH$_2$).

EXAMPLE 20

Histamine Derivatisation of maleic anhydride-alt-isobutylene copolymer

Maleic anhydride-alt-isobutylene copolymer (2.000 g, 13 mmol unit) was dissolved in DMF (60 ml) at ambient temperature. A solution of histamine (1.441 g, 13 mmol) in DMF (15 ml) was added dropwise at ambient temperature. The solution was left to stand for 1 h. The solution was rotary evaporated to dryness, via a gel phase, to produce a homogeneous white powder. Yield 3.44 g, 100%. IR (cast film, KBr disc)/cm$^{-1}$: Amide; 1652, 1556.

$^1$H-NMR (270 MHz, d$_7$-DMF, ppm): 8.50 (1H, Ar); 7.15 (1H, Ar); 3.40 (br, 2H, CH); 2.90-1.20 (multiple conformational, 6H, CH$_2$); 1.00-0.60 (multiple conformational, 6H, CH$_3$).

EXAMPLE 21

Histamine Derivatisation of maleic anhydride-alt-styrene copolymer

Maleic anhydride-alt-styrene copolymer (2.623 g, 13 mmol unit) was dissolved in DMF (60 ml) at ambient temperature. A solution of histamine (1.441 g, 13 mmol) in DMF (15 ml) was added dropwise at ambient temperature.

The solution was left to stand for 1 h, during which time gelation occurred. The gel was rotary evaporated to dryness to produce a homogeneous white powder.

Yield 4.06 g, 100%. IR (cast film, KBr disc)/cm$^{-1}$: Amide; 1652, 1556.

$^1$H-NMR (270 MHz, d$_7$-DMF, ppm): 8.30 (br, 1H, Ar); 7.15 (br, 1H, Ar); 6.85 (br, 5H, Ar); 3.50-1.00 (multiple conformational, 9H).

EXAMPLE 22

Histamine Derivatisation of maleic anhydride-alt-methyl vinyl ether copolymer Maleic anhydride-alt-methylvinylether copolymer (2.026 g, 13 mmol unit) was dissolved in DMF (60 ml) at ambient temperature. A solution of histamine (1.441 g, 13 mmol) in DMF (15 ml) was added dropwise at ambient temperature. The solution was left to stand for 1 h, during which time gelation occurred. The gel was rotary evaporated to dryness to produce a homogeneous white powder.

Yield 3.47 g, 100%. IR (cast film, KBr disc)/cm$^{-1}$: Amide; 1650, 1553.

$^1$H-NMR (270 MHz, d$_7$-DMF, ppm): 8.50 (1H, Ar); 7.25 (1H, Ar); 4.00-2.50 (multiple conformational, 8H); 1.75 (br, 3H, CH$_3$).

EXAMPLE 23

Histamine Derivatisation of maleic anhydride-alt-n-butylvinylether copolymer Maleic anhydride-alt-n-butylvinylether copolymer (2.571 g, 13 mmol unit) was dissolved in DMF (60 ml) at ambient temperature. A solution of histamine (1.441 g, 13 mmol) in DMF (15 ml) was added dropwise at ambient temperature. The gel was left to stand for 1 h. The gel was rotary evaporated to dryness, via a gel phase, to produce a homogeneous white powder. Yield 4.01 g, 100%. IR (cast film, KBr disc)/cm$^{-1}$: Amide; 1697, 1557.

$^1$H-NMR (270 MHz, d$_7$-DMF, ppm): 8.55 (1H, Ar); 7.25 (1H, Ar); 4.30-1.00 (multiple conformational, 14H); 0.70 (br, 3H, CH$_3$).

EXAMPLE 24

2-aminoethanethiol Derivatisation of maleic anhydride-alt-isobutylene copolymer Maleic anhydride-alt-isobutylene copolymer (4.011 g, 26 mmol unit) was dissolved in DMF (70 ml) at 100° C. Sodium borohydride (1.000 g, 26 mmol) was added. A heated solution of 2-aminoethanethiol.HCl (3.020 g, 26 mmol) in DMF (10 ml) was added dropwise followed by a solution of triethylamine (2.663 g, 26 mmol) in DMF (5 ml) added dropwise. The solution was stirred for 1 h at 100° C. followed by a further 4 h stirring at ambient temperature. The resulting viscous solution was poured into 1M HCl (500 ml) to precipitate a white product. The product was filtered, washed with distilled water, dried by suction and further dried overnight in a vacuum desiccator. Yield 4.717 g, 78%. IR (cast film, KBr disc)/cm$^{-1}$: Amide; 1736, 1655.

EXAMPLE 25

2-aminoethanethiol Derivatisation of maleic anhydride-alt-styrene copolymer

Maleic anhydride-alt-styrene copolymer (2.580 g, 13 mmol unit) was dissolved in DMF (50 ml) at 100° C. Sodium borohydride (0.510 g, 13 mmol) was added. A heated solution of 2-aminoethanethiol.HCl (1.460 g, 13 mmol) in DMF (5 ml) was added dropwise followed by a solution of triethylamine (1.300 g, 13 mmol) in DMF (5 ml) added dropwise. The solution was stirred for 1 h at 100° C. followed by a further 4 h stirring at ambient temperature. The resulting viscous solution was poured into 1M HCl (250 ml) to precipitate a white product. The product was filtered, washed with distilled water, dried by suction and further dried overnight in a vacuum desiccator. Yield 3.510 g, 85%. IR (cast film, KBr disc)/cm$^{-1}$: Amide; 1725, 1658.

EXAMPLE 26

2-aminoethanethiol Derivatisation of methylmaleic anhydride-alt-styrene copolymer Methylmaleic anhydride-alt-styrene copolymer (2.628 g, 12 mmol unit) was dissolved in DMF (50 ml) at 100° C. Sodium borohydride (0.480 g, 12 mmol) was added. A heated solution of 2-aminoethanethiol.HCl (1.380 g, 12 mmol) in DMF (5 ml) was added dropwise followed by a solution of triethylamine (1.230 g, 12 mmol) in DMF (5 ml) added dropwise.

The solution was stirred for 1 h at 100° C. followed by a further 4 h stirring at ambient temperature. The resulting viscous solution was poured into 1M HCl (250 ml) to precipitate a white product. The product was filtered, washed with distilled water, dried by suction and further dried overnight in a vacuum desiccator. Yield 2.500 g, 62%. IR (cast film, KBr disc)/cm$^{-1}$: Amide; 1702, 1658.

EXAMPLE 27

2-aminoethanethiol Derivatisation of phenylmaleic anhydride-alt-styrene copolymer Phenylmaleic anhydride-alt-styrene copolymer (2.367 g, 9 mmol unit) was dissolved in DMF (50 ml) at 100° C. Sodium borohydride (0.340 g, 9 mmol) was added. A heated solution of 2-aminoethanethiol.HCl (0.974 g, 9 mmol) in DMF (5 ml) was added dropwise followed by a solution of triethylamine (0.871 g, 9 mmol) in DMF (5 ml) added dropwise. The solution was stirred for 1 h at 100° C. followed by a further 4 h stirring at ambient temperature. The resulting viscous solution was poured into 1M HCl (250 ml) to precipitate a white product. The product was filtered, washed with distilled water, dried by suction and further dried overnight in a vacuum desiccator. Yield 2.794 g, 93%. IR (cast film, KBr disc)/cm$^{-1}$: Amide; 1706, 1656.

EXAMPLE 28

2-aminoethanethiol Derivatisation of maleic anhydride-alt-n-butylvinylether copolymer Maleic anhydride-alt-n-butylvinylether copolymer (2.500 g, 12 mmol unit) was dissolved in DMF (50 ml) at 100° C. Sodium borohydride (0.500 g, 12 mmol) was added. A heated solution of 2-aminoethanethiol.HCl (1.450 g, 12 mmol) in DMF (5 ml) was added dropwise followed by a solution of triethylamine (1.280 g, 12 mmol) in DMF (5 ml) added dropwise. The solution was stirred for 1 h at 100° C. followed by a further 4 h stirring at ambient temperature. The resulting viscous solution was poured into 1M HCl (250 ml) to precipitate a white product. The product was filtered, washed with distilled water, dried by suction and further dried overnight in a vacuum desiccator. Yield 2.310 g, 66%. IR (cast film, KBr disc)/cm$^{-1}$: Amide; 1704, 1658.

EXAMPLE 29

2-aminoethanethiol Derivatisation of methylmaleic anhydride-alt-n-butylvinylether copolymer Methylmaleic anhydride-alt-n-butylvinylether copolymer (2.540 g, 12 mmol unit) was dissolved in DMF (50 ml) at 100° C. Sodium borohydride (0.500 g, 12 mmol) was added. A heated solution of 2-aminoethanethiol.HCl (1.356 g, 12 mmol) in DMF (5 ml) was added dropwise followed by a solution of triethylamine (1.209 g, 12 mmol) in DMF (5 ml) added dropwise. The solution was stirred for 1 h at 100° C. followed by a further 4 h stirring at ambient temperature. The resulting viscous solution was poured into 1M HCl (250 ml) to precipitate a white product. The product was filtered, washed with distilled water, dried by suction and further dried overnight in a vacuum desiccator. Yield 2.190 g, 63%. IR (cast film, KBr disc)/cm$^{-1}$: Amide; 1723, 1654.

EXAMPLE 30

2-(2-aminoethyl)-pyridine Derivatisation of maleic anhydride-alt-methylvinylether copolymer Maleic anhydride-alt-methylvinylether copolymer (0.201 g, 1.3 mmol unit) was dissolved in DMF (60 ml) at ambient temperature. A solution of 2-(2-aminoethyl)-pyridine (0.152 g, 1.3 mmol) in DMF (5 ml) was added dropwise at ambient temperature. The solution was left to stir for 4 h. The solution was rotary evaporated to dryness to produce a homogeneous powder. Yield 0.353 g, 100%. IR (cast film, KBr disc)/cm$^{-1}$: Amide; 1650, 1553.
$^{1}$H-NMR (270 MHz, D$_2$O, ppm): 8.60 (1H, Ar); 8.30 (1H, Ar); 7.70 (1H, Ar); 4.00-2.50 (multiple conformational, 9H); 1.75 (br, 3H, CH$_3$).

EXAMPLE 31

1-(3-aminopropyl)imidazole Derivatisation of maleic anhydride-alt-methylvinylether copolymer Maleic anhydride-alt-methylvinylether copolymer (2.000 g, 12.8 mmol unit) was dissolved in DMF (100 ml) at ambient temperature. A solution of 1-(3-aminopropyl)imidazole (1.603 g, 12.8 mmol) in DMF (5 ml) was added dropwise at ambient temperature. The solution was left to stir for 4 h. The solution was rotary evaporated to dryness to produce a homogeneous powder. Yield 3.603 g, 100%. IR (cast film, KBr disc)/cm$^{-1}$: Amide; 1650, 1553.
$^{1}$H-NMR (270 MHz, D$_2$O, ppm): 8.70 (1H, Ar); 7.50 (1H, Ar); 7.45 (1H, Ar); 4.00-2.50 (multiple conformational, 11H); 1.50 (br, 3H, CH$_3$).

EXAMPLE 32

N-(2-aminoethyl)pyrrolidine Derivatisation of maleic anhydride-alt-methylvinylether copolymer Maleic anhydride-alt-methylvinylether copolymer (0.980 g, 6.3 mmol unit) was dissolved in DMF (60 ml) at ambient temperature. A solution of N-(2-aminoethyl)pyrrolidine (0.717 g, 6.3 mmol) in DMF (5 ml) was added dropwise at ambient temperature. The solution was left to stir for 4 h.
The solution was rotary evaporated to dryness to produce a homogeneous powder. Yield 1.697 g, 100%. IR (cast film, KBr disc)/cm$^{-1}$: Amide; 1650, 1553.

EXAMPLE 33

2-(2-aminoethyl)-5-nitropyridine Derivatisation of maleic anhydride-alt-methylvinylether copolymer Maleic anhydride-alt-methylvinylether copolymer (1.004 g, 6.4 mmol unit) was dissolved in DMF (60 ml) at ambient temperature. A solution of 2-(2-aminoethyl)-5-nitropyridine (1.171 g, 6.4 mmol) in DMF (5 ml) was added dropwise at ambient temperature. The solution was left to stir for 4 h. The solution was rotary evaporated to dryness to produce a homogeneous powder. Yield 2.175 g, 100%. IR (cast film, KBr disc)/cm$^{-1}$: Amide; 1650, 1553.
$^{1}$H-NMR (270 MHz, d$_7$-DMF, ppm): 8.80 (1H, Ar); 8.00 (1H, Ar); 6.65 (1H, Ar); 4.00-2.50 (multiple conformational, 9H); 1.90 (br, 3H, CH$_3$).

EXAMPLE 34

N-(3'-aminopropyl)pyrrolidinone Derivatisation of maleic anhydride-alt-methylvinylether copolymer Maleic anhydride-alt-methylvinylether copolymer (2.000 g, 12.8 mmol unit) was dissolved in DMF (60 ml) at ambient temperature. A solution of N-(3'-aminopropyl)pyrrolidinone (1.821 g, 12.8 mmol) in DMF (5 ml) was added dropwise at ambient temperature. The solution was left to stir for 4 h. The solution was rotary evaporated to dryness to produce a homogeneous powder. Yield 3.821 g, 100%. IR (cast film, KBr disc)/cm$^{-1}$: Amide; 1650, 1553.

EXAMPLE 35

Condensation of Histamine Derivative of maleic anhydride-alt-methylvinylether copolymer (Example 22)

The polymer produced in Example 22 was heated to 210° C. under high vacuum. Water vapour was seen to be evolved.

EXAMPLE 36

Condensation of Histamine Derivative of maleic anhydride-alt-n-butylvinylether Copolymer (Example 23)

The polymer produced in Example 23 was heated to 210° C. under high vacuum. Water vapour was seen to be evolved. The resulting purple powder was desiccated for storage. Imide; 1769, 1691. UV-vis $\lambda_{max}$ 620 nm.

EXAMPLE 37

Condensation of 2-(2-aminoethyl)-pyridine Derivative of maleic anhydride-alt-methyl vinyl ether copolymer (Example 30)

The polymer produced in Example 30 was heated to 210° C. under high vacuum. Water vapour was seen to be evolved. The resulting blue powder was desiccated for storage. IR (KBr disc)/cm$^{-1}$: Imide; 1769, 1691. UV-vis $\lambda_{max}$ 568 nm.

EXAMPLE 38

Condensation of 1-(3-aminopropyl)imidazole Derivative of maleic anhydride-alt-methyl vinyl ether copolymer (Example 31)

The polymer produced in Example 31 was heated to 210° C. under high vacuum. Water vapour was seen to be evolved. The resulting blue powder was desiccated for storage. IR (KBr disc)/cm$^{-1}$: Imide; 1769, 1691. UV-vis $\lambda_{max}$ 586 nm.

EXAMPLE 39

Condensation of N-(2-aminoethyl)pyrrolidine Derivative of maleic anhydride-alt-methyl vinyl ether copolymer (Example 32)

The polymer produced in Example 32 was heated to 210° C. under high vacuum. Water vapour was seen to be evolved. The resulting blue powder was desiccated for storage. IR (KBr disc)/cm$^{-1}$: Imide; 1769, 1691. UV-vis $\lambda_{max}$ 576 nm.

EXAMPLE 40

Condensation of 2-(2-aminoethyl)-5-nitropyridine Derivative of maleic anhydride-alt-methyl vinyl ether copolymer (Example 33)

The polymer produced in Example 33 was heated to 210° C. under high vacuum. Water vapour was seen to be evolved. The resulting powder was desiccated for storage. IR (KBr disc)/cm$^{-1}$: Imide; 1769, 1691.

EXAMPLE 41

Condensation of N-(3'-aminopropyl)pyrrolidinone Derivative of maleic anhydride-alt-methyl vinyl ether copolymer (Example 34)

The polymer produced in Example 34 was heated to 210° C. under high vacuum. Water vapour was seen to be evolved. The resulting blue powder was desiccated for storage. IR (KBr disc)/cm$^{-1}$: Imide; 1769, 1691. UV-vis $\lambda_{max}$ 572 nm.

Activity of Functional Copolymers

Examples 1-41 provide various methods for the attachment of novel functions to alternating copolymers of maleic anhydride. The unexpected benefits that attachment to alternating copolymers of maleic anhydride brings to the actives are exemplified below:

EXAMPLE 42

The polymer produced in Example 14 is the conjugate of a serine protease inhibitor (4-(2-aminoethyl)benzenesulphonylfluoride—AEBSF) and maleic anhydride-alt-isobutylene copolymer. The inhibitory performance of AEBSF and the conjugate (Example 14) was assessed against the serine proteases trypsin, thrombin and elastase on a unit per unit basis (see FIG. 1). IC$_{50}$ values were obtained from the experimental data presented in FIG. 1.

| Enzyme [C] | IC$_{50}$ [μM] AEBSF | IC$_{50}$ [μM] Example 14 |
|---|---|---|
| Trypsin (4.0 μg/ml) | 61.1 | 6.1 |
| Elastase (1.2 μg/ml) | 312.5 | 1.1 |
| Thrombin (2.0 μg/ml) | 712.3 | 1.4 |

20° C., 0.2M TRIS buffer

Example 14 is 280-times more effective than AEBSF in the inhibition of elastase.

Example 14 is 10-times more effective than AEBSF in the inhibition of trypsin.

Example 14 is 500-times more effective than AEBSF in the inhibition of thrombin.

The solution lifetime of chemically active inhibitors like AEBSF can be extremely short due to their high reactivity. The solution stability (0.2M TRIS, 20° C.) of Example 14 and AEBSF were compared by assaying their respective trypsin inhibition activities with ageing time, see FIG. 2. Over an 8-hour period, the inhibitive capacity of AEBSF fell exponentially toward zero. In the same period, the inhibitive capacity of Example 14 fell by only 5%.

The high chemical reactivity of protease inhibitors represents toxicological problems both in vitro and potentially in vivo. The cytotoxicity of AEBSF and Example 14 were assessed in vitro on a culture of ovine meniscal chondrocytes P3 with a 48 h incubation time. DNA concentrations were obtained using a PicoGreen assay. The results of this assay are presented in FIG. 3. AEBSF begins to exhibit significant toxicity deviation from the vehicle alone at a concentration of 8 μg/ml.

Example 14 begins to exhibit significant toxicity deviation from the vehicle alone at a concentration of 250 μg/ml. Example 14 is 30-times less toxic, in this assay, than AEBSF.

Protease inhibitors are commonly assessed by their capability to eliminate proteolytic activity from solutions containing only the target protease and a specific substrate (see above and FIG. 1). To assess the suitability of Example 14 in a more realistic environment, an elastase inhibition assay was carried out in excess heat inactivated foetal calf serum (HIFCS). The results of this assay are presented in FIG. 4. The positive control activity of elastase drops to 20% of that in the absence of HIFCS and the $IC_{50}$ for Example 14 rises to 65.7 nmol/ml under these conditions.

In summary, Example 14 out-performs AEBSF in several significant ways: increased activity, increased lifetime and lower cytotoxicity. The physical, chemical and biological properties of the conjugated inhibitor can be rapidly modified applying structural variants such as Examples 15-18.

EXAMPLE 43

The polymer produced in Example 10 is a conjugate of the neurotransmitter 3-hydroxytyramine (dopamine) and maleic anhydride-alt-isobutylene copolymer. The structure of dopamine contains a catechol moiety that exhibits excellent anti-oxidant and metal ion-sequestering ability. Unfortunately, dopamine undergoes extremely rapid auto-oxidation in aqueous media and this can negate many potential applications.

The aqueous solution lifetime of dopamine was compared to Example 6,

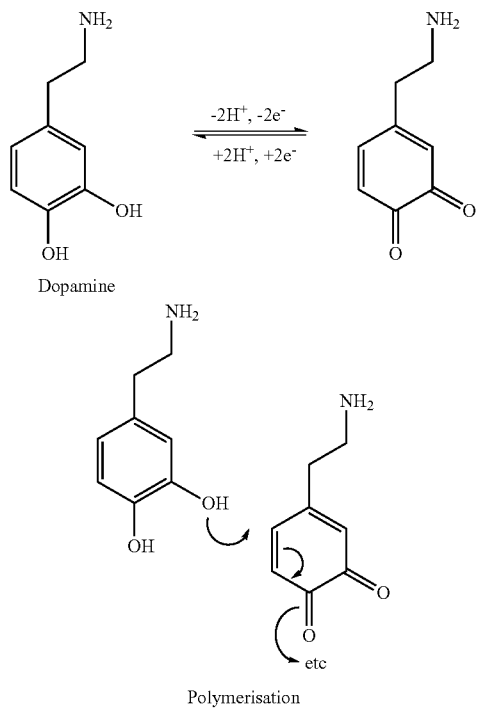

Polymerisation

Example 10 and Example 11 at a concentration of 8.6 mM in 0.2 M TRIS (pH 8). The resulting oxidative processes were recorded by UV-vis spectrometry, see FIG. 5. The rate of auto-oxidation was slowed by 24-fold in Examples 6, 10 and 11 compared to dopamine.

The differing structure of the polymer scaffold allows straightforward selection of physicochemical properties, such as solubility. To demonstrate this, Examples 6, 10 and 11 were compared for precipitation threshold in ferrous solutions of varying concentration. The catechol moiety present in all these polymers acts as a sacrificial reductant and maintains the ferrous state of the iron, preventing conversion to ferric ions. 100 μl of 8.65 mM polymer solution (made up in 0.2 mM TRIS pH 8) was added to 1 ml of iron (II) chloride solution (made up in distilled water). The solution was left to stand for 30 min. and checked for precipitation of an intensely coloured purple complex. The minimum ferrous concentrations required for precipitation are recorded below:

| Polymer | Iron(II)chloride/μM | Concentration ratio Fe(II)/Polymer |
|---|---|---|
| Example 6 | 3.12 | 3.6 |
| Example 10 | 2.66 | 3.1 |
| Example 11 | 2.38 | 2.8 |

The catechol moiety is also able to sequester ferric ions in a tris(catechol) hexadentate complex. To ensure that this ability was not compromised in the polymer conjugate a UV-vis titration of Examples 6, 10 and 11 was carried out with ferrous ions. To 1 ml of 0.865 mM solution (made up in 0.2M TRIS pH 8) of each example, 20 μl aliquots of 2.84 mM ferrous chloride (made up in distilled water) were added up to 100 μl. For each increment, the UV-vis absorbance was recorded at 495 nm. The final molar ratio in this experiment was 3 catechol per iron ion. The UV-vis results are shown in FIG. 6. Iron sequestration was linear for all examples in the concentration range tested.

EXAMPLE 44

Heparin Complexation to Example 20

The polymers produced in Examples 19-23 are conjugates of histamine maleic anhydride-alternating copolymers. Histamine was utilised as a precursor for the specific presentation of imidazole appendages. The imidazole group is specifically recognised by several glycosaminoglycans (GAGs) including heparin. GAGs are themselves recognised specifically by an enormous range of functional biomolecules including enzymes such as antithrombin. GAG recognition regulates the activity of these biomolecules. Hence, by applying Examples 19-23 as GAG scaffolds, one can produce hybrid materials designed to regulate biochemical processes.

To this end, a solution of Example 22 (100 mg, 433 mmol unit) in 0.5 M HCl (5 ml) was added dropwise to a solution of heparin (250 mg, 433 mmol unit) in 0.5 M HCl (5 ml). Immediate complexation occurred, causing the formation of an elastic mass, phase separated from the solvent. The mass could be separated and deformed, see FIG. 7.

To probe this complexation, a polymeric fluorescent reporting moiety (5-(2-aminoethylamino)-1-naphthalene sulphonic acid, sodium salt conjugated to maleic anhydride-alt-isobutylene copolymer) was substituted for heparin. In this case, addition of Example 22 caused the formation of a phase-separated complex with shifted emission wavelength (green to blue), see FIG. 8.

A further rational synthesis of this complex can ould be achieved at neutral pH followed by solvent removal. The complex can ould be rendered water insoluble by further conversion of poly(amic acid) to poly(imide) by dehydration (see Example 35).

Applications

The following examples describe applications of the materials of the present invention.

EXAMPLE 45

Laser Printing to Produced Selective Cell Tissue Scaffolds

The physicochemical attributes of Examples 22 and 35, Examples 23 and 36, Examples 30 and 37, Examples 31 and 38, Examples 32 and 39, Examples 33 and 40 and Examples 34 and 41 vary markedly depending upon the conversion of amic acid units to imide units:

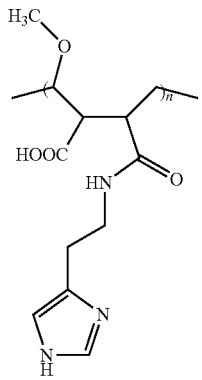
EXAMPLE 22

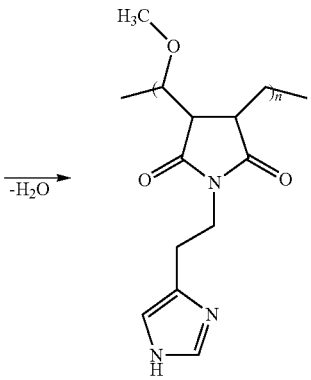
EXAMPLE 30

For example, the water solubilisation of Example 22 is rapid while Example 30 is insoluble in water. The extent of conversion of amic acid to imide for the polymer as a whole defines the material on the intervening solubility range. Hence the solubility of the material can be varied independently of the attached functional group.

The differential water solubilities or hydration characteristics of the amic acid and imide variants can be tuned to allow or prevent cell attachment.

For example, the imides (Examples 35 and 36) provide a good scaffold for cell attachment while the amic acids (Examples 22 and 23) prevent cell attachment, see FIG. 9. These observations led us to develop a novel method for the designation of areas of cell attachment on the surface, or throughout a device.

6 mm diameter discs of Example 23 (15 mg) were cold compression moulded between polished stainless steel polished (Graseby Specac) under a pressure of 2 tonnes.

Discs were heated at designated locations by a perpendicular laser source, providing sufficient heat (200-210° C.) for the amic acid to imide conversion reaction. A suitable laser source was a 25 W $CO_2$ laser running at 2% power tracking at 200 mm/s with a 0.17 s marking time. The design so produced, see FIG. 10, is limited in minimum size only by the spatial resolution of the laser beam. Hence, it is possible to designate the location of individual cells by this method.

Exposure of the so produced disc to a suspension of human dermal fibroblast cells results in cell attachment to the designated area only, FIG. 10.

This is a rapid method of providing specific molecular structural alterations on the surface of a material. This method offers specific advantages when compared to plasma treatment, self-assembled monolayers or lithographic techniques.

EXAMPLE 46

Dialysis Button

Polymeric conjugates of biochemically active species offer an attractive means of providing local therapies, while isolating the active from the local environment. This can be achieved by retaining the polymeric conjugate behind a dialysis membrane of suitable molecular weight cut off (MWCO). The MWCO must be lower than the weight of the polymeric conjugate, to cause retention, and higher than the species to be interacted with, to allow perfusion through the membrane.

A suitable system for biological applications applies a polymeric conjugate of the highest possible molecular weight and a membrane with MWCO as close as possible to this but still eliminating transport of the conjugate. In this manner, the majority of biomolecules, including: ions, peptides and proteins can easily pass back and forth through the membrane. The polymeric conjugate is then free to interact with its target.

To demonstrate this, the preparation of Example 10 was repeated with the substitution of 5-(2-aminoethylamino)-1-naphthalene sulphonic acid, sodium salt for 1% of the 3-hydroxytyramine, producing a fluorescent conjugate (493 nm emission), see FIG. 11. This material was dissolved at a concentration of 10 mg/ml in 0.2 M TRIS pH 8. 100 µl of this solution was contained inside a dialysis button (Hampton Research, Laguna Niguel, U.S.A) by a 7000 MWCO dialysis membrane (Snakeskin, Perbio, Rockford, U.S.A.), FIG. 11.

Each button so prepared was placed upright in sodium periodate solution (5 ml, 94 mM).

The buttons were allowed to dialyse for varying times, up to 28 minutes at 25° C. without agitation. After this time, an image was captured of the dialysis buttons, FIG. 12. The perfusion of periodate through the 7000 MWCO dialysis membrane achieved complete oxidation of the catechol moieties of the polymer conjugate within 28 minutes.

This demonstrated that the buttons work, even in a static environment.

Dialysis devices of this sort can be applied topically, for example to wounds, or implanted for localised therapy, for example adjacent to osteoporotic bone or bone fractures or soft tissue lesions, for dialysis in situ.

EXAMPLE 47

Protective Cream

Example 18 was formulated into a cream for topical skin applications as follows: Nikkomulese 41 (2.5%), Dimethicone (1.5%), Crodamol GTCC (2.0%) and Sepigel 305 (3.5%) were mixed and heated to 75° C. To this was added water (40%) heated to 75° C. This mixture was cooled to 35° C. To this was added pre-mixed Example 18 (1.4%), polyol prepolymer 2 (2%), water (41.9%), quaternium 15 (0.2%) and Tinocare GL (5%). Zinc oxide may be added at up to 30% content to adjust handling characteristics.

The resulting preparations can be applied topically for the neutralisation of detrimental protease activity (for example, from urine or faeces) without significant dermal penetration.

EXAMPLE 48

Reducing Gels

The polymers produced in Examples 24-29 are conjugates of 2-aminoethanethiol and maleic anhydride alternating copolymers. Such systems have been previously prepared as disulfide bridge-reducing supports (T. Otsu, S. Aoki, R. Nakatani, *Makromol. Chem.*, 1970, 134, 331.). We aimed to provide a gel material with the ability to reduce glutathione dimer (GS-SG) to glutathione monomer (GSH) for therapeutic benefit in topical, for example wound, and internal, for example atherosclerotic, applications.

Example 26 (242 mg, 0.7 mmol unit) was converted to the corresponding sodium by immersion in an equimolar solution of sodium hydroxide (29 mg, 0.7 mmol) in distilled water (10 ml). The resulting gel was separated and washed repeatedly with distilled water (5×10 ml). Weighed samples of gel were transferred to transwell inserts for testing. Human dermal fibroblasts were seeded at 60000 cells per well in DMEM with 10% foetal calf serum (800 µl). The gel-containing transwells were then placed in each well and to each well was added an aliquot of hydrogen peroxide (300 µl, 5.866 mmol $dm^{-3}$). This volume of hydrogen peroxide was known to result total cell death. The plate was incubated for 24 h. The wells were washed with phosphate buffered saline and 200 µl distilled water was added to the cells. The cells were frozen and the DNA content determined by standard PicoGreen assay. The resulting DNA concentrations are tabulated below:

|  | DNA concentration (µg/ml) | Cell viability (%) |
|---|---|---|
| DMEM + 10% FCS | 14.804 | (100) |
| 0 mg sodium salt of Example 24 | 2.244 | 15 |
| 100 mg sodium salt of Example 24 | 8.268 | 56 |
| 200 mg sodium salt of Example 24 | 16.429 | 111 |
| 300 mg sodium salt of Example 24 | 16.197 | 109 |
| 400 mg sodium salt of Example 24 | 15.055 | 102 |
| 500 mg sodium salt of Example 24 | 15.275 | 103 |
| 600 mg sodium salt of Example 24 | 15.953 | 108 |

In the absence of the sodium salt of Example 24, 15% of the fibroblasts are viable after 24 h in the presence of hydrogen peroxide. In contrast, addition of gel masses in excess of 200 mg results in 100% cell viability over the same period.

EXAMPLE 49

Tissue Engineering Scaffold

The preparation of highly porous three-dimensional constructs for tissue engineering applications requires specialised techniques (for example, the use of blowing agents or super-critical $CO_2$). It would be advantageous if constructs could be manufactured without the need of these additional chemicals and processes. The conversion of poly(amic acid) derivatives (such as Examples 1-29) to poly(imide) derivatives (such as Examples 35-41), with the evolution of water, provides a means of meeting this requirement. For example, powdered Example 22 (100 mg) was placed in a PTFE tube (6 mm diam.) and heated to 210° C. The water evolved during the condensation reaction acted as a blowing agent and the result was a highly porous plug of Example 35, FIG. 13. The so produced scaffold was seeded with human dermal fibroblasts at a density of 2 million cells (200 µl) and incubated for 6 days. The cell-seeded material was visualised by confocal microscopy with live-dead cell staining, FIG. 14.

EXAMPLE 50

Self-Forming Devices

The technology described in Example 45 can be applied to produce devices that, when swollen with aqueous fluids, take on a final shape dictated by the surface, or internally created design (in two or three dimensions). As a demonstration, 6 mm diameter discs of Example 22 were heated by laser (see Example 45) to create parallel lines upon each flat surface (FIG. 15). The sets of parallel lines were arranged perpendicular to each other on opposing faces of the disc. When immersed in an aqueous fluid, expansion was constrained by the laser design and a mechanically predicted 'saddle' was the result (FIG. 15). This technology can be developed to create many varied final device shapes.

The invention claimed is:

1. An artefact comprising a medical device selected from a solid medical implant device or scaffold, a solid medical device suitable for management of the body as an implant inside the body, or outside the body, and a medical device for cell attachment and directed cell movement, comprising an alternating copolymer comprising a backbone derived from a maleic anhydride compound and an alkene compound, wherein the backbone is the result of alternating radical copolymerisation of maleic anhydride compound with alkene compound, wherein the copolymer also comprises moieties of an active compound containing a nucleophilic group selected from an alcohol, thiol, isocyanate or amine group, bound to the backbone at the anhydride moiety by a moiety of the nucleophilic group, wherein the backbone is derived from maleic anhydride compounds (A) and alkene compounds (B):

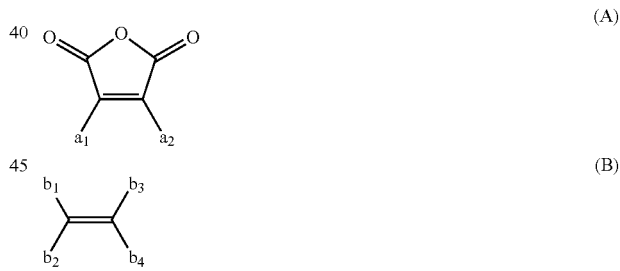

wherein the maleic anhydride compound of formula (A) is selected from:
maleic anhydride;
alkyl and cycloalkyl substituted derivatives thereof; and
aryl substituted derivatives thereof; and the alkene compound (B) is selected from:
alkene;
alkoxyl substituted derivatives thereof and their ester derivatives;
alkanoyloxy substituted derivatives thereof;
aryl substituted derivatives thereof, or wherein
$a_1$ is a proton, $a_2$ is a proton, methyl or phenyl substituent, $b_1$ and $b_2$ are protons, and $b_3$ and $b_4$ are methyl substituents; or $b_3$ is a proton and $b_4$ is linear aliphatic, phenyl, or linear or branched alkoxyl, optionally substituted with hydroxyl or alkanoyloxl or alkanoyloxyl, or wherein at least one of $a_1$ and $a_2$ is an electron-withdrawing species while at least one of $b_1$, $b_2$, $b_3$, and $b_4$ is an electron-donating species or vice versa, wherein electron-withdrawing species $a_1$ and $a_2$ or $b_1$, $b_2$, $b_3$ and $b_4$ are selected from alka(poly)alkenyl, $C_{6-10}$ aryl, $C_{1-24}$ alkoxyl, $C_{1-24}$ alkylthio, $C_{1-6}$ alkanoyloxy, $C_{1-6}$ alkoxycarbonyl, all of which may be substituted with an electron-withdrawing substituent; and wherein electron-donating species $b_1$, $b_2$, $b_3$ and $b_4$ or $a_1$ and $a_2$ as appropriate, include $C_{1-6}$ alkyl which can have a linear or branched structure and $C_{4-9}$ cycloalkyl.

2. The artefact of claim 1 wherein a solid medical device suitable for management of the body outside the body is in the form of a film, foam, coating, fibre or monolith including articles for the in situ purification of bodily fluids outside the body, an ultrafiltration artefact including coatings and membranes used for ex situ purification of bodily fluids.

3. The artefact of claim 1 which is a dialysis membrane fabricated into a device for internal and external medical applications.

4. The artefact of claim 1 in the form of a film, foam, coating, fibre or monolith suitable for management of the local biological environment, internal or external.

5. The artefact of claim 1 incorporated in medicinal wound delivery means or wound coverings or including medicinal compositions suitable for management of the wound environment in situ or ex situ.

6. The artefact of claim 1 which includes medicinal compositions suitable for management of a wound environment and/or bodily fluids ex situ in dialysis.

7. The artefact of claim 1 wherein the copolymer is a poly(amic acid).

8. The artefact of claim 1 wherein the copolymer is a poly(imide).

9. The artefact of claim 1, wherein the active compound contains an amine group and the copolymer is a poly(amic acid) and comprises maleimide moieties.

10. The artefact of claim 1 wherein the active compound contains an amine group and the copolymer is a poly(amic acid) and comprises maleimide moieties wherein colour is an indication of conversion of poly(amic acid) to poly(imide).

11. The artefact of claim 1 wherein the alternating copolymer contains the terminal structural motif:

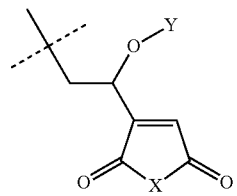

where X is O, NH or NR; and
Y is an alkyl.

12. An artefact comprising an alternating copolymer comprising a backbone derived from a maleic anhydride compound and an alkene compound, wherein the backbone is the result of alternating radical copolymerisation of maleic anhydride compound with alkene compound, wherein the copolymer also comprises moieties of an active compound containing a nucleophilic group selected from an alcohol, thiol, isocyanate or amine group, bound to the backbone at the anhydride moiety by a moiety of the nucleophilic group, wherein the backbone is derived from maleic anhydride compounds (A) and alkene compounds (B):

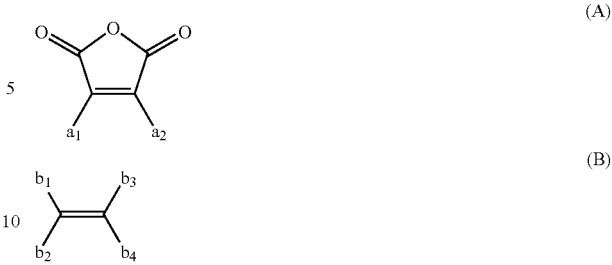

wherein at least one of $a_1$ and $a_2$ is an electron-withdrawing species while at least one of $b_1$, $b_2$, $b_3$, and $b_4$ is an electron-donating species or vice versa, wherein electron-withdrawing species $a_1$ and $a_2$ or $b_1$, $b_2$, $b_3$ and $b_4$ are selected from alka(poly)alkenyl, $C_{6-10}$ aryl, $C_{1-24}$ alkoxyl, $C_{1-24}$ alkylthio, $C_{1-6}$ alkanoyloxy, $C_{1-6}$ alkoxycarbonyl, all of which may be substituted with an electron-withdrawing substituent; and wherein electron-donating species $b_1$, $b_2$, $b_3$ and $b_4$ or $a_1$ and $a_2$ as appropriate, include $C_{1-6}$ alkyl which can have a linear or branched structure and $C_4$ cycloalkyl.

13. The artefact of claim 12 selected from a medical dressing or a fluid adhesive or medicinal composition, and a medical device selected from a solid medical implant device or scaffold, a solid medical device suitable for management of the body as an implant inside the body, or outside the body, and a medical device for cell attachment and directed cell movement.

14. The artefact of claim 12 wherein the copolymer is a poly(amic acid).

15. The artefact of claim 12 wherein the copolymer is a poly(imide).

16. The artefact of claim 12, wherein the active compound contains an amine group and the copolymer is a poly(amic acid) and comprises maleimide moieties.

17. The artefact of claim 12 wherein the active compound contains an amine group and the copolymer is a poly(amic acid) and comprises maleimide moieties wherein colour is an indication of conversion of poly(amic acid) to poly(imide).

18. The artefact of claim 12 wherein the alternating copolymer contains the terminal structural motif:

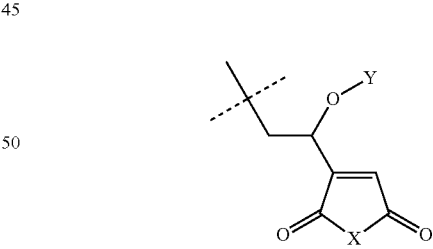

where X is O, NH or NR; and
Y is an alkyl.

19. An artefact comprising a medical device selected from a solid medical implant device or scaffold, a solid medical device suitable for management of the body as an implant inside the body, or outside the body, and a medical device for cell attachment and directed cell movement, comprising an alternating copolymer comprising a backbone derived from a maleic anhydride compound and an alkene compound, wherein the backbone is the result of alternating radical copolymerisation of maleic anhydride compound with alkene compound, wherein the copolymer also comprises moieties of an active compound containing a nucleophilic group selected from an alcohol, thiol, isocyanate or amine group, bound to the backbone at the anhydride moiety by a moiety of the nucleophilic group, wherein the copolymer is a poly(amic acid).

20. The artefact of claim 19, wherein the active compound contains an amine group and the copolymer is a poly(amic acid) and comprises maleimide moieties.

21. The artefact of claim 19 wherein the active compound contains an amine group and the copolymer is a poly(amic acid) and comprises maleimide moieties wherein colour is an indication of conversion of poly(amic acid) to poly(imide).

22. The artefact of claim 19 wherein the alternating copolymer contains the terminal structural motif:

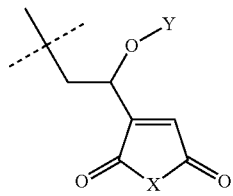

where X is O, NH or NR; and
Y is an alkyl.

23. A method for manufacturing a medical device for cell attachment and directed cell movement comprising a poly (amic acid) alternating copolymer having poly(imide) moieties, comprising a backbone derived from a maleic anhydride compound and an alkene compound, wherein the backbone is the result of alternating radical copolymerisation of maleic anhydride compound with alkene compound, wherein the copolymer also comprises moieties of an active compound containing a amine nucleophilic group bound to the backbone at the anhydride moiety by a moiety of the nucleophilic group, said method comprising:
 (1) laser heating the poly(amic acid) alternating copolymer to create chemical modifications and designate surface characteristics on a micrometer scale to designate areas allowing or disallowing cell attachment, or
 (2) laser heating the poly(amic acid) alternating copolymer to create chemical modifications and thereby create a surface design or internally created design in two or three dimensions.

24. The method according to claim 23 comprising immersing the laser heated copolymer in aqueous fluids, whereby the copolymer swells and takes on a final shape dictated by the surface design, or the internally created design in two or three dimensions, by means of differential expansion by fluid uptake which is constrained by the laser design to produce a mechanically predicted conformation.

25. The method of claim 23 wherein colour is an indication of conversion of poly(amic acid) to poly(imide).

\* \* \* \* \*